US009945872B2

(12) United States Patent
Flora et al.

(10) Patent No.: US 9,945,872 B2
(45) Date of Patent: Apr. 17, 2018

(54) BIOMARKERS OF LUNG FUNCTION

(75) Inventors: Jason Flora, Richmond, VA (US); Barbara K. Zedler, Richmond, VA (US); Edward Lenn Murrelle, Midlothian, VA (US); Mark Leppert, Salt Lake City, UT (US); Edwin J. C. G. van den Oord, Richmond, VA (US); Bradley Todd Webb, Richmond, VA (US); Timothy York, Richmond, VA (US); Gaurav S. J. B. Rana, Richmond, VA (US); Jeffrey S. Edmiston, Mechanicsville, VA (US); Willie J. McKinney, Richmond, VA (US)

(73) Assignee: Lineagen, Inc., Salt Lake City, UT (US)

(*) Notice: Subject to any disclaimer, the term of this patent is extended or adjusted under 35 U.S.C. 154(b) by 1086 days.

(21) Appl. No.: 13/541,462

(22) Filed: Jul. 3, 2012

(65) Prior Publication Data

US 2013/0149389 A1 Jun. 13, 2013

Related U.S. Application Data

(63) Continuation of application No. PCT/US2011/020151, filed on Jan. 4, 2011.

(Continued)

(51) Int. Cl.
*G01N 33/68* (2006.01)
*C40B 40/10* (2006.01)
(Continued)

(52) U.S. Cl.
CPC ......... *G01N 33/6893* (2013.01); *C07H 21/00* (2013.01); *C07K 17/00* (2013.01);
(Continued)

(58) Field of Classification Search
CPC .......... G01N 33/6893; G01N 33/6848; G01N 2800/12; G01N 2800/60; G01N 2800/122;
(Continued)

(56) References Cited

U.S. PATENT DOCUMENTS

2008/0044843 A1 2/2008 Perlee et al.
2008/0227117 A1 9/2008 Fehniger et al.

FOREIGN PATENT DOCUMENTS

WO WO-2008/003066 1/2008

OTHER PUBLICATIONS

Bhattacharya et al. (American Journal of Respiratory Cell and Molecular Biology, 2008, 40:359-367).*
Lacoma et al. (Eur. Respir. Rev., 2009; 18: 112, pp. 96-104).*
Anderson et al. (Molecular & Cellular Proteomics 5.4 (2006): 573-588).*
International Search Report and Written Opinion in International Application No. PCT/US11/20151, dated May 2, 2011, 12 pages.
Supplementary European Search Report, Application No. EP 11728575; dated Oct. 21, 2013, 7 pages.

(Continued)

*Primary Examiner* — Jeremy C Flinders
(74) *Attorney, Agent, or Firm* — Perkins Coie LLP

(57) ABSTRACT

Cigarette smoking is a primary determinant of chronic obstructive pulmonary disease (COPD), which is the fourth leading cause of morbidity and mortality in the United States. Unique proteins associated with COPD capable of differentiating subjects likely to experience rapid (RPD) or slow (SLW) decline in lung function have been identified using comprehensive high-throughput proteomic approaches. Thirty peptides, which mapped to 21 unique proteins, were linearly associated with annualized rates of lung function decline among smokers with COPD characterized as having rapid or slow decline and smokers without COPD. Using three different statistical approaches to assess the data, the RPD and SLW groups are differentiated by 55 peptides, which mapped to 33 unique proteins. A number of the identified peptides are proteolytic fragments of proteins that are involved in the complement and/or coagulation systems, have anti-protease activity, or metabolic functions.

21 Claims, 3 Drawing Sheets

Related U.S. Application Data

(60) Provisional application No. 61/292,151, filed on Jan. 4, 2010.

(51) Int. Cl.
  *C07K 17/00* (2006.01)
  *C07H 21/00* (2006.01)
  *C40B 40/08* (2006.01)
  C40B 20/02 (2006.01)
  G01N 33/574 (2006.01)

(52) U.S. Cl.
  CPC .............. *C40B 40/08* (2013.01); *C40B 40/10* (2013.01); *C40B 20/02* (2013.01); *G01N 33/57423* (2013.01); *G01N 33/6848* (2013.01); *G01N 2800/12* (2013.01); *G01N 2800/122* (2013.01); *G01N 2800/60* (2013.01)

(58) Field of Classification Search
  CPC .. G01N 33/57423; C40B 40/08; C40B 40/10; C40B 20/02; C07K 17/00
  See application file for complete search history.

(56) References Cited

OTHER PUBLICATIONS

Seung-Ha Lee et al: "Complement C3a and C4a Increased in Plasma of Patients with Aspirin-induced Asthma", American Journal of Respiratory and Critical Care Medicine, vol. 173. No. 4, Feb. 15, 2006, pp. 370-378.

T. Rhim et al: "Plasma protein profiles in early asthmatic responses to inhalation allergen challenge", Allergy, vol. 64, No. 1, Jan. 1, 2009, pp. 47-54.

York Timothy P et al: "High-resolution mass spectrometry proteomics for the identification of candidate plasma protein biomarkers for chronic obstructive pulmonary disease". Biomarkers, Taylor and Francis, London, GB. vol. 15, No. 4, Jun. 1, 2010, pp. 367-377.

Gaurav S J B Rana et al: "Proteomic biomarkers in plasma that differentiate rapid and slow decline in lung function in adult cigarette smokers with chronic obstructive pulmonary disease (COPD)", Analytical and Bioanalytical Chemistry, Springer, Berlin, DE, vol. 397, No. 5, May 5, 2010, pp. 1809-1819.

\* cited by examiner

SEQUENCE LISTING

```
<160> NUMBER OF SEQ ID NOS: 16

<210> SEQ ID NO 1
<211> LENGTH: 1741
<212> TYPE: PRT
<213> ORGANISM: Homo sapiens

<400> SEQUENCE: 1

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
```

```
                275                 280                 285
Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ile Ile Glu Ser Pro Gly Gly Glu Met
                340                 345                 350

Glu Glu Ala Glu Leu Thr Ser Trp Tyr Phe Val Ser Ser Pro Phe Ser
                355                 360                 365

Leu Asp Leu Ser Lys Thr Lys Arg His Leu Val Pro Gly Ala Pro Phe
        370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Ala Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
        435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
                500                 505                 510

Gly Gln Ile Val Phe Met Asn Arg Glu Pro Lys Arg Thr Leu Thr Ser
        515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
        595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
                660                 665                 670

Lys Thr Thr Arg Lys Lys Arg Asn Val Asn Phe Gln Lys Ala Ile Asn
        675                 680                 685

Glu Lys Leu Gly Gln Tyr Ala Ser Pro Thr Ala Lys Arg Cys Cys Gln
690                 695                 700
```

```
Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
        740                 745                 750

Gly Leu Gln Arg Ala Leu Glu Ile Leu Gln Glu Asp Leu Ile Asp
    755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
        835                 840                 845

Leu Glu Leu Arg Pro Val Leu Tyr Asn Tyr Leu Asp Lys Asn Leu Thr
    850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
        915                 920                 925

Lys Val Leu Gln Ile Glu Lys Glu Gly Ala Ile His Arg Glu Glu Leu
    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val  Ala Ser Leu Leu Arg  Leu Pro Arg
        995                 1000                 1005

Gly Cys  Gly Glu Gln Thr Met  Ile Tyr Leu Ala Pro  Thr Leu Ala
    1010                 1015                 1020

Ala Ser Arg Tyr Leu Asp Lys  Thr Glu Gln Trp Ser  Thr Leu Pro
    1025                 1030                 1035

Pro Glu  Thr Lys Asp His Ala  Val Asp Leu Ile Gln  Lys Gly Tyr
    1040                 1045                 1050

Met Arg  Ile Gln Gln Phe Arg  Lys Ala Asp Gly Ser  Tyr Ala Ala
    1055                 1060                 1065

Trp Leu  Ser Arg Asp Ser Ser  Thr Trp Leu Thr Ala  Phe Val Leu
    1070                 1075                 1080

Lys Val  Leu Ser Leu Ala Gln  Glu Gln Val Gly Gly  Ser Pro Glu
    1085                 1090                 1095

Lys Leu  Gln Glu Thr Ser Asn  Trp Leu Leu Ser Gln  Gln Gln Ala
    1100                 1105                 1110
```

-continued

Asp Gly Ser Phe Gln Asp Pro Cys Pro Val Leu Asp Arg Ser Met
1115                1120                1125

Gln Gly Gly Leu Val Gly Asn Asp Glu Thr Val Ala Leu Thr Ala
1130                1135                1140

Phe Val Thr Ile Ala Leu His His Gly Leu Ala Val Phe Gln Asp
1145                1150                1155

Glu Gly Ala Glu Pro Leu Lys Gln Arg Val Glu Ala Ser Ile Ser
1160                1165                1170

Lys Ala Asn Ser Phe Leu Gly Glu Lys Ala Ser Ala Gly Leu Leu
1175                1180                1185

Gly Ala His Ala Ala Ala Ile Thr Ala Tyr Ala Leu Ser Leu Thr
1190                1195                1200

Lys Ala Pro Val Asp Leu Leu Gly Val Ala His Asn Asn Leu Met
1205                1210                1215

Ala Met Ala Gln Glu Thr Gly Asp Asn Leu Tyr Trp Gly Ser Val
1220                1225                1230

Thr Gly Ser Gln Ser Asn Ala Val Ser Pro Thr Pro Ala Pro Arg
1235                1240                1245

Asn Pro Ser Asp Pro Met Pro Gln Ala Pro Ala Leu Trp Ile Glu
1250                1255                1260

Thr Thr Ala Tyr Ala Leu Leu His Leu Leu His Glu Gly Lys
1265                1270                1275

Ala Glu Met Ala Asp Gln Ala Ser Ala Trp Leu Thr Arg Gln Gly
1280                1285                1290

Ser Phe Gln Gly Gly Phe Arg Ser Thr Gln Asp Thr Val Ile Ala
1295                1300                1305

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Tyr Asp Glu Leu Pro Ala Lys Asp Asp Pro
1415                1420                1425

Asp Ala Pro Leu Gln Pro Val Thr Pro Leu Gln Leu Phe Glu Gly
1430                1435                1440

Arg Arg Asn Arg Arg Arg Glu Ala Pro Lys Val Val Glu Glu
1445                1450                1455

Gln Glu Ser Arg Val His Tyr Thr Val Cys Ile Trp Arg Asn Gly
1460                1465                1470

Lys Val Gly Leu Ser Gly Met Ala Ile Ala Asp Val Thr Leu Leu
1475                1480                1485

Ser Gly Phe His Ala Leu Arg Ala Asp Leu Glu Lys Leu Thr Ser
1490                1495                1500

Leu Ser Asp Arg Tyr Val Ser His Phe Glu Thr Glu Gly Pro His

-continued

```
            1505                1510                1515

Val Leu Leu Tyr Phe Asp Ser Val Pro Thr Ser Arg Glu Cys Val
    1520                1525                1530

Gly Phe Glu Ala Val Gln Glu Val Pro Val Gly Leu Val Gln Pro
    1535                1540                1545

Ala Ser Ala Thr Leu Tyr Asp Tyr Tyr Asn Pro Glu Arg Arg Cys
    1550                1555                1560

Ser Val Phe Tyr Gly Ala Pro Ser Lys Ser Arg Leu Leu Ala Thr
    1565                1570                1575

Leu Cys Ser Ala Glu Val Cys Gln Cys Ala Glu Gly Lys Cys Pro
    1580                1585                1590

Arg Gln Arg Arg Ala Leu Glu Arg Gly Leu Gln Asp Glu Asp Gly
    1595                1600                1605

Tyr Arg Met Lys Phe Ala Cys Tyr Tyr Pro Arg Val Glu Tyr Gly
    1610                1615                1620

Phe Gln Val Lys Val Leu Arg Glu Asp Ser Arg Ala Ala Phe Arg
    1625                1630                1635

Leu Phe Glu Thr Lys Ile Thr Gln Val Leu His Phe Thr Lys Asp
    1640                1645                1650

Val Lys Ala Ala Ala Asn Gln Met Arg Asn Phe Leu Val Arg Ala
    1655                1660                1665

Ser Cys Arg Leu Arg Leu Glu Pro Gly Lys Glu Tyr Leu Ile Met
    1670                1675                1680

Gly Leu Asp Gly Ala Thr Tyr Asp Leu Glu Gly His Pro Gln Tyr
    1685                1690                1695

Leu Leu Asp Ser Asn Ser Trp Ile Glu Glu Met Pro Ser Glu Arg
    1700                1705                1710

Leu Cys Arg Ser Thr Arg Gln Arg Ala Ala Cys Ala Gln Leu Asn
    1715                1720                1725

Asp Phe Leu Gln Glu Tyr Gly Thr Gln Gly Cys Gln Val
    1730                1735                1740

<210> SEQ ID NO 2
<211> LENGTH: 433
<212> TYPE: PRT
<213> ORGANISM: Homo sapiens

<400> SEQUENCE: 2

Met Glu Arg Met Leu Pro Leu Ala Leu Gly Leu Leu Ala Ala Gly
1                5                  10                 15

Phe Cys Pro Ala Val Leu Cys His Pro Asn Ser Pro Leu Asp Glu Glu
                20                  25                 30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Leu Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Ala Ser Ser Ser Pro His Gly Asp Leu Leu Arg
            100                 105                 110

Gln Lys Phe Thr Gln Ser Phe Gln His Leu Arg Ala Pro Ser Ile Ser
        115                 120                 125
```

```
Ser Ser Asp Glu Leu Gln Leu Ser Met Gly Asn Ala Met Phe Val Lys
    130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Pro Asp Ser Gln Thr Met Met Val Leu Val
        195                 200                 205

Asn Tyr Ile Phe Phe Lys Ala Lys Trp Glu Met Pro Phe Asp Pro Gln
210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Val Val Ser Asp Val Phe Glu Glu
        355                 360                 365

Gly Thr Glu Ala Ser Ala Ala Thr Ala Val Lys Ile Thr Leu Leu Ser
370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Ser Lys Pro Arg Ala Cys Ile Lys Gln Trp Gly Ser
            420                 425                 430

Gln

<210> SEQ ID NO 3
<211> LENGTH: 202
<212> TYPE: PRT
<213> ORGANISM: Homo sapiens

<400> SEQUENCE: 3

Met Leu Pro Pro Gly Thr Ala Thr Leu Leu Thr Leu Leu Leu Ala Ala
1               5                   10                  15

Gly Ser Leu Gly Gln Lys Pro Gln Arg Pro Arg Arg Pro Ala Ser Pro
            20                  25                  30

Ile Ser Thr Ile Gln Pro Lys Ala Asn Phe Asp Ala Gln Gln Phe Ala
        35                  40                  45

Gly Thr Trp Leu Leu Val Ala Val Gly Ser Ala Cys Arg Phe Leu Gln
50                  55                  60
```

```
Glu Gln Gly His Arg Ala Glu Ala Thr Thr Leu His Val Ala Pro Gln
 65                  70                  75                  80

Gly Thr Ala Met Ala Val Ser Thr Phe Arg Lys Leu Asp Gly Ile Cys
                 85                  90                  95

Trp Gln Val Arg Gln Leu Tyr Gly Asp Thr Gly Val Leu Gly Arg Phe
            100                 105                 110

Leu Leu Gln Ala Arg Gly Ala Arg Gly Ala Val Asn Val Val Ala
            115                 120                 125

Glu Thr Asp Tyr Gln Ser Phe Ala Val Leu Tyr Leu Glu Arg Ala Gly
        130                 135                 140

Gln Leu Ser Val Lys Leu Tyr Ala Arg Ser Leu Pro Val Ser Asp Ser
145                 150                 155                 160

Val Leu Ser Gly Phe Glu Gln Arg Val Gln Glu Ala His Leu Thr Glu
                165                 170                 175

Asp Gln Ile Phe Tyr Phe Pro Lys Tyr Gly Phe Cys Glu Ala Ala Asp
            180                 185                 190

Gln Phe His Val Leu Asp Glu Val Arg Arg
            195                 200

<210> SEQ ID NO 4
<211> LENGTH: 427
<212> TYPE: PRT
<213> ORGANISM: Homo sapiens

<400> SEQUENCE: 4

Met Ala Leu Leu Trp Gly Leu Val Leu Ser Trp Ser Cys Leu Gln
 1               5                  10                  15

Gly Pro Cys Ser Val Phe Ser Pro Val Ser Ala Met Glu Pro Leu Gly
                 20                  25                  30

Arg Gln Leu Thr Ser Gly Pro Asn Gln Glu Gln Val Ser Pro Leu Thr
            35                  40                  45

Leu Leu Lys Leu Gly Asn Gln Val Gln Pro Gly Ala Gln Asn His Thr
        50                  55                  60

Leu Gln Arg Leu Gln Gln Val Leu His Ala Gly Ser Gly Pro Cys Leu
65                  70                  75                  80

Pro His Leu Leu Ser Arg Leu Cys Gln Asp Leu Gly Pro Gly Ala Phe
                 85                  90                  95

Arg Leu Ala Ala Arg Met Tyr Leu Gln Lys Gly Phe Pro Ile Lys Glu
            100                 105                 110

Asp Phe Leu Glu Gln Ser Glu Gln Leu Phe Gly Ala Lys Pro Val Ser
        115                 120                 125

Leu Thr Gly Lys Gln Glu Asp Asp Leu Ala Asn Ile Asn Gln Trp Val
130                 135                 140

Lys Glu Ala Thr Glu Gly Lys Ile Gln Glu Phe Leu Ser Gly Leu Pro
145                 150                 155                 160

Glu Asp Thr Val Leu Leu Leu Leu Asn Ala Ile His Phe Gln Gly Phe
                165                 170                 175

Trp Arg Asn Lys Phe Asp Pro Ser Leu Thr Gln Arg Asp Ser Phe His
            180                 185                 190

Leu Asp Glu Gln Phe Thr Val Pro Val Glu Met Met Gln Ala Arg Thr
        195                 200                 205

Tyr Pro Leu Arg Trp Phe Leu Leu Glu Gln Pro Glu Ile Gln Val Ala
210                 215                 220

His Phe Pro Phe Lys Asn Asn Met Ser Phe Val Val Leu Val Pro Thr
225                 230                 235                 240
```

His Phe Glu Trp Asn Val Ser Gln Val Leu Ala Asn Leu Ser Trp Asp
                245                 250                 255

Thr Leu His Pro Pro Leu Val Trp Glu Arg Pro Thr Lys Val Arg Leu
            260                 265                 270

Pro Lys Leu Tyr Leu Lys His Gln Met Asp Leu Val Ala Thr Leu Ser
        275                 280                 285

Gln Leu Gly Leu Gln Glu Leu Phe Gln Ala Pro Asp Leu Arg Gly Ile
    290                 295                 300

Ser Glu Gln Ser Leu Val Val Ser Gly Val Gln His Gln Ser Thr Leu
305                 310                 315                 320

Glu Leu Ser Glu Val Gly Val Glu Ala Ala Ala Thr Ser Ile Ala
                325                 330                 335

Met Ser Arg Met Ser Leu Ser Ser Phe Ser Val Asn Arg Pro Phe Leu
                340                 345                 350

Phe Phe Ile Phe Glu Asp Thr Thr Gly Leu Pro Leu Phe Val Gly Ser
            355                 360                 365

Val Arg Asn Pro Asn Pro Ser Ala Pro Arg Glu Leu Lys Glu Gln Gln
        370                 375                 380

Asp Ser Pro Gly Asn Lys Asp Phe Leu Gln Ser Leu Lys Gly Phe Pro
385                 390                 395                 400

Arg Gly Asp Lys Leu Phe Gly Pro Asp Leu Lys Leu Val Pro Pro Met
                405                 410                 415

Glu Glu Asp Tyr Pro Gln Phe Gly Ser Pro Lys
                420                 425

<210> SEQ ID NO 5
<211> LENGTH: 263
<212> TYPE: PRT
<213> ORGANISM: Homo sapiens

<400> SEQUENCE: 5

Met Gln Arg Ala Arg Pro Thr Leu Trp Ala Ala Cys Glu Pro Cys Asp
1               5                   10                  15

Ala Arg Ala Leu Ala Gln Cys Ala Pro Pro Ala Val Cys Ala Glu
            20                  25                  30

Leu Val Arg Glu Pro Gly Cys Gly Cys Cys Leu Thr Cys Ala Leu Ser
        35                  40                  45

Glu Gly Gln Pro Cys Gly Ile Tyr Thr Glu Arg Cys Gly Ser Gly Leu
    50                  55                  60

Arg Cys Gln Pro Ser Pro Asp Glu Ala Arg Pro Leu Gln Ala Leu Leu
65                  70                  75                  80

Asp Gly Arg Gly Leu Cys Val Asn Ala Ser Ala Val Ser Arg Leu Arg
                85                  90                  95

Ala Tyr Leu Leu Pro Ala Pro Pro Ala Pro Gly Asn Ala Ser Glu Ser
            100                 105                 110

Glu Glu Asp Arg Ser Ala Gly Ser Val Glu Ser Pro Ser Val Ser Ser
        115                 120                 125

Thr His Arg Val Ser Asp Pro Lys Phe His Pro Leu His Ser Lys Ile
    130                 135                 140

Ile Ile Ile Lys Lys Gly His Ala Lys Asp Ser Gln Arg Tyr Lys Val
145                 150                 155                 160

Asp Tyr Glu Ser Gln Ser Thr Asp Thr Gln Asn Phe Ser Ser Glu Ser
                165                 170                 175

Lys Arg Glu Thr Glu Tyr Gly Pro Cys Arg Arg Glu Met Glu Asp Thr

```
                    180                 185                 190
Leu Asn His Leu Lys Phe Leu Asn Val Leu Ser Pro Arg Gly Val His
            195                 200                 205

Ile Pro Asn Cys Asp Lys Lys Gly Phe Tyr Lys Lys Gln Cys Arg
    210                 215                 220

Pro Ser Lys Gly Arg Lys Arg Gly Phe Cys Trp Cys Val Asp Lys Tyr
225                 230                 235                 240

Gly Gln Pro Leu Pro Gly Tyr Thr Thr Lys Gly Lys Glu Asp Val His
                245                 250                 255

Cys Tyr Ser Met Gln Ser Lys
                260

<210> SEQ ID NO 6
<211> LENGTH: 605
<212> TYPE: PRT
<213> ORGANISM: Homo sapiens

<400> SEQUENCE: 6

Met Ala Leu Arg Lys Gly Gly Leu Ala Leu Ala Leu Leu Leu Leu Ser
1               5                   10                  15

Trp Val Ala Leu Gly Pro Arg Ser Leu Glu Gly Ala Asp Pro Gly Thr
            20                  25                  30

Pro Gly Glu Ala Glu Gly Pro Ala Cys Pro Ala Ala Cys Val Cys Ser
        35                  40                  45

Tyr Asp Asp Asp Ala Asp Glu Leu Ser Val Phe Cys Ser Ser Arg Asn
    50                  55                  60

Leu Thr Arg Leu Pro Asp Gly Val Pro Gly Gly Thr Gln Ala Leu Trp
65                  70                  75                  80

Leu Asp Gly Asn Asn Leu Ser Ser Val Pro Pro Ala Ala Phe Gln Asn
                85                  90                  95

Leu Ser Ser Leu Gly Phe Leu Asn Leu Gln Gly Gly Gln Leu Gly Ser
            100                 105                 110

Leu Glu Pro Gln Ala Leu Leu Gly Leu Glu Asn Leu Cys His Leu His
        115                 120                 125

Leu Glu Arg Asn Gln Leu Arg Ser Leu Ala Leu Gly Thr Phe Ala His
    130                 135                 140

Thr Pro Ala Leu Ala Ser Leu Gly Leu Ser Asn Asn Arg Leu Ser Arg
145                 150                 155                 160

Leu Glu Asp Gly Leu Phe Glu Gly Leu Gly Ser Leu Trp Asp Leu Asn
                165                 170                 175

Leu Gly Trp Asn Ser Leu Ala Val Leu Pro Asp Ala Ala Phe Arg Gly
            180                 185                 190

Leu Gly Ser Leu Arg Glu Leu Val Leu Ala Gly Asn Arg Leu Ala Tyr
        195                 200                 205

Leu Gln Pro Ala Leu Phe Ser Gly Leu Ala Glu Leu Arg Glu Leu Asp
    210                 215                 220

Leu Ser Arg Asn Ala Leu Arg Ala Ile Lys Ala Asn Val Phe Val Gln
225                 230                 235                 240

Leu Pro Arg Leu Gln Lys Leu Tyr Leu Asp Arg Asn Leu Ile Ala Ala
                245                 250                 255

Val Ala Pro Gly Ala Phe Leu Gly Leu Lys Ala Leu Arg Trp Leu Asp
            260                 265                 270

Leu Ser His Asn Arg Val Ala Gly Leu Leu Glu Asp Thr Phe Pro Gly
        275                 280                 285
```

```
Leu Leu Gly Leu Arg Val Leu Arg Leu Ser His Asn Ala Ile Ala Ser
        290                 295                 300

Leu Arg Pro Arg Thr Phe Lys Asp Leu His Phe Leu Glu Glu Leu Gln
305                 310                 315                 320

Leu Gly His Asn Arg Ile Arg Gln Leu Ala Glu Arg Ser Phe Glu Gly
                325                 330                 335

Leu Gly Gln Leu Glu Val Leu Thr Leu Asp His Asn Gln Leu Gln Glu
            340                 345                 350

Val Lys Ala Gly Ala Phe Leu Gly Leu Thr Asn Val Ala Val Met Asn
        355                 360                 365

Leu Ser Gly Asn Cys Leu Arg Asn Leu Pro Glu Gln Val Phe Arg Gly
    370                 375                 380

Leu Gly Lys Leu His Ser Leu His Leu Glu Gly Ser Cys Leu Gly Arg
385                 390                 395                 400

Ile Arg Pro His Thr Phe Thr Gly Leu Ser Gly Leu Arg Arg Leu Phe
                405                 410                 415

Leu Lys Asp Asn Gly Leu Val Gly Ile Glu Glu Gln Ser Leu Trp Gly
            420                 425                 430

Leu Ala Glu Leu Leu Glu Leu Asp Leu Thr Ser Asn Gln Leu Thr His
        435                 440                 445

Leu Pro His Arg Leu Phe Gln Gly Leu Gly Lys Leu Glu Tyr Leu Leu
    450                 455                 460

Leu Ser Arg Asn Arg Leu Ala Glu Leu Pro Ala Asp Ala Leu Gly Pro
465                 470                 475                 480

Leu Gln Arg Ala Phe Trp Leu Asp Val Ser His Asn Arg Leu Glu Ala
                485                 490                 495

Leu Pro Asn Ser Leu Leu Ala Pro Leu Gly Arg Leu Arg Tyr Leu Ser
            500                 505                 510

Leu Arg Asn Asn Ser Leu Arg Thr Phe Thr Pro Gln Pro Pro Gly Leu
        515                 520                 525

Glu Arg Leu Trp Leu Glu Gly Asn Pro Trp Asp Cys Gly Cys Pro Leu
    530                 535                 540

Lys Ala Leu Arg Asp Phe Ala Leu Gln Asn Pro Ser Ala Val Pro Arg
545                 550                 555                 560

Phe Val Gln Ala Ile Cys Glu Gly Asp Asp Cys Gln Pro Pro Ala Tyr
                565                 570                 575

Thr Tyr Asn Asn Ile Thr Cys Ala Ser Pro Pro Glu Val Val Gly Leu
            580                 585                 590

Asp Leu Arg Asp Leu Ser Glu Ala His Phe Ala Pro Cys
        595                 600                 605

<210> SEQ ID NO 7
<211> LENGTH: 742
<212> TYPE: PRT
<213> ORGANISM: Homo sapiens

<400> SEQUENCE: 7

Met Glu Lys Leu Phe Cys Cys Phe Pro Asn Ser Met Val Val Glu His
1               5                   10                  15

Pro Glu Phe Leu Lys Ala Gly Lys Glu Pro Gly Leu Gln Ile Trp Arg
            20                  25                  30

Val Glu Lys Phe Asp Leu Val Pro Val Pro Thr Asn Leu Tyr Gly Asp
        35                  40                  45

Phe Phe Thr Gly Asp Ala Tyr Val Ile Leu Lys Thr Val Gln Leu Arg
    50                  55                  60
```

```
Asn Gly Asn Leu Gln Tyr Asp Leu His Tyr Trp Leu Gly Asn Glu Cys
 65                  70                  75                  80

Ser Gln Asp Glu Ser Gly Ala Ala Ala Ile Phe Thr Val Gln Leu Asp
                 85                  90                  95

Asp Tyr Leu Asn Gly Arg Ala Val Gln His Arg Glu Val Gln Gly Phe
            100                 105                 110

Glu Ser Ala Thr Phe Leu Gly Tyr Phe Lys Ser Gly Leu Lys Tyr Lys
        115                 120                 125

Lys Gly Gly Val Ala Ser Gly Phe Lys His Val Val Pro Asn Glu Val
    130                 135                 140

Val Val Gln Arg Leu Phe Gln Val Lys Gly Arg Arg Val Val Arg Ala
145                 150                 155                 160

Thr Glu Val Pro Val Ser Trp Glu Ser Phe Asn Asn Gly Asp Cys Phe
                165                 170                 175

Ile Leu Asp Leu Gly Asn Asn Ile His Gln Trp Cys Gly Ser Asn Ser
            180                 185                 190

Asn Arg Tyr Glu Arg Leu Lys Ala Thr Gln Val Ser Lys Gly Ile Arg
        195                 200                 205

Asp Asn Glu Arg Ser Gly Arg Ala Arg Val His Val Ser Glu Glu Gly
    210                 215                 220

Thr Glu Pro Glu Ala Met Leu Gln Val Leu Gly Pro Lys Pro Ala Leu
225                 230                 235                 240

Pro Ala Gly Thr Glu Asp Thr Ala Lys Glu Asp Ala Ala Asn Arg Lys
                245                 250                 255

Leu Ala Lys Leu Tyr Lys Val Ser Asn Gly Ala Gly Thr Met Ser Val
            260                 265                 270

Ser Leu Val Ala Asp Glu Asn Pro Phe Ala Gln Gly Ala Leu Lys Ser
        275                 280                 285

Glu Asp Cys Phe Ile Leu Asp His Gly Lys Asp Gly Lys Ile Phe Val
    290                 295                 300

Trp Lys Gly Lys Gln Ala Asn Thr Glu Glu Arg Lys Ala Ala Leu Lys
305                 310                 315                 320

Thr Ala Ser Asp Phe Ile Thr Lys Met Asp Tyr Pro Lys Gln Thr Gln
                325                 330                 335

Val Ser Val Leu Pro Glu Gly Gly Glu Thr Pro Leu Phe Lys Gln Phe
            340                 345                 350

Phe Lys Asn Trp Arg Asp Pro Asp Gln Thr Asp Gly Leu Gly Leu Ser
        355                 360                 365

Tyr Leu Ser Ser His Ile Ala Asn Val Glu Arg Val Pro Phe Asp Ala
    370                 375                 380

Ala Thr Leu His Thr Ser Thr Ala Met Ala Ala Gln His Gly Met Asp
385                 390                 395                 400

Asp Asp Gly Thr Gly Gln Lys Gln Ile Trp Arg Ile Glu Gly Ser Asn
                405                 410                 415

Lys Val Pro Val Asp Pro Ala Thr Tyr Gly Gln Phe Tyr Gly Gly Asp
            420                 425                 430

Ser Tyr Ile Ile Leu Tyr Asn Tyr Arg His Gly Gly Arg Gln Gly Gln
        435                 440                 445

Ile Ile Tyr Asn Trp Gln Gly Ala Gln Ser Thr Gln Asp Glu Val Ala
    450                 455                 460

Ala Ser Ala Ile Leu Thr Ala Gln Leu Asp Glu Glu Leu Gly Gly Thr
465                 470                 475                 480
```

```
Pro Val Gln Ser Arg Val Val Gln Gly Lys Glu Pro Ala His Leu Met
            485                 490                 495

Ser Leu Phe Gly Gly Lys Pro Met Ile Ile Tyr Lys Gly Gly Thr Ser
        500                 505                 510

Arg Glu Gly Gly Gln Thr Ala Pro Ala Ser Thr Arg Leu Phe Gln Val
            515                 520                 525

Arg Ala Asn Ser Ala Gly Ala Thr Arg Ala Val Glu Val Leu Pro Lys
        530                 535                 540

Ala Gly Ala Leu Asn Ser Asn Asp Ala Phe Val Leu Lys Thr Pro Ser
545                 550                 555                 560

Ala Ala Tyr Leu Trp Val Gly Thr Gly Ala Ser Glu Ala Glu Lys Thr
                565                 570                 575

Gly Ala Gln Glu Leu Leu Arg Val Leu Arg Ala Gln Pro Val Gln Val
            580                 585                 590

Ala Glu Gly Ser Glu Pro Asp Gly Phe Trp Glu Ala Leu Gly Gly Lys
        595                 600                 605

Ala Ala Tyr Arg Thr Ser Pro Arg Leu Lys Asp Lys Lys Met Asp Ala
            610                 615                 620

His Pro Pro Arg Leu Phe Ala Cys Ser Asn Lys Ile Gly Arg Phe Val
625                 630                 635                 640

Ile Glu Glu Val Pro Gly Glu Leu Met Gln Glu Asp Leu Ala Thr Asp
                645                 650                 655

Asp Val Met Leu Leu Asp Thr Trp Asp Gln Val Phe Val Trp Val Gly
            660                 665                 670

Lys Asp Ser Gln Glu Glu Lys Thr Glu Ala Leu Thr Ser Ala Lys
        675                 680                 685

Arg Tyr Ile Glu Thr Asp Pro Ala Asn Arg Asp Arg Arg Thr Pro Ile
            690                 695                 700

Thr Val Val Lys Gln Gly Phe Glu Pro Pro Ser Phe Val Gly Trp Phe
705                 710                 715                 720

Leu Gly Trp Asp Asp Asp Tyr Trp Ser Val Pro Leu Asp Arg Ala
                725                 730                 735

Met Ala Glu Leu Ala Ala
            740

<210> SEQ ID NO 8
<211> LENGTH: 253
<212> TYPE: PRT
<213> ORGANISM: Homo sapiens

<400> SEQUENCE: 8

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65              70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110
```

-continued

His Asp Leu Leu Leu Gln Leu Ser Glu Lys Ala Thr Leu Gly Pro
            115                 120                 125

Ala Val Arg Pro Leu Pro Trp Gln Arg Val Asp Arg Asp Val Ala Pro
        130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205

Gly Gly Pro Leu Val Cys Gly Gly Val Leu Glu Gly Val Val Thr Ser
210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 9
<211> LENGTH: 2355
<212> TYPE: PRT
<213> ORGANISM: Homo sapiens

<400> SEQUENCE: 9

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr

```
            225                 230                 235                 240
        Arg Ile Gly Asp Thr Trp Ser Lys Lys Asp Asn Arg Gly Asn Leu Leu
                            245                 250                 255

Gln Cys Ile Cys Thr Gly Asn Gly Arg Gly Glu Trp Lys Cys Glu Arg
                            260                 265                 270

His Thr Ser Val Gln Thr Thr Ser Gly Ser Gly Pro Phe Thr Asp
                        275                 280                 285

Val Arg Ala Ala Val Tyr Gln Pro Gln Pro His Pro Gln Pro Pro Pro
        290                 295                 300

Tyr Gly His Cys Val Thr Asp Ser Gly Val Val Tyr Ser Val Gly Met
        305                 310                 315                 320

Gln Trp Leu Lys Thr Gln Gly Asn Lys Gln Met Leu Cys Thr Cys Leu
                            325                 330                 335

Gly Asn Gly Val Ser Cys Gln Glu Thr Ala Val Thr Gln Thr Tyr Gly
                        340                 345                 350

Gly Asn Ser Asn Gly Glu Pro Cys Val Leu Pro Phe Thr Tyr Asn Gly
                        355                 360                 365

Arg Thr Phe Tyr Ser Cys Thr Thr Glu Gly Arg Gln Asp Gly His Leu
        370                 375                 380

Trp Cys Ser Thr Thr Ser Asn Tyr Glu Gln Asp Gln Lys Tyr Ser Phe
        385                 390                 395                 400

Cys Thr Asp His Thr Val Leu Val Gln Thr Arg Gly Gly Asn Ser Asn
                        405                 410                 415

Gly Ala Leu Cys His Phe Pro Phe Leu Tyr Asn Asn His Asn Tyr Thr
                    420                 425                 430

Asp Cys Thr Ser Glu Gly Arg Arg Asp Asn Met Lys Trp Cys Gly Thr
                    435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
        465                 470                 475                 480

Gly Asp Gln Trp Asp Lys Gln His Asp Met Gly His Met Met Arg Cys
                        485                 490                 495

Thr Cys Val Gly Asn Gly Arg Gly Glu Trp Thr Cys Ile Ala Tyr Ser
                    500                 505                 510

Gln Leu Arg Asp Gln Cys Ile Val Asp Asp Ile Thr Tyr Asn Val Asn
                    515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
        545                 550                 555                 560

Cys Gln Asp Ser Glu Thr Gly Thr Phe Tyr Gln Ile Gly Asp Ser Trp
                        565                 570                 575

Glu Lys Tyr Val His Gly Val Arg Tyr Gln Cys Tyr Cys Tyr Gly Arg
                    580                 585                 590

Gly Ile Gly Glu Trp His Cys Gln Pro Leu Gln Thr Tyr Pro Ser Ser
                    595                 600                 605

Ser Gly Pro Val Glu Val Phe Ile Thr Glu Thr Pro Ser Gln Pro Asn
                610                 615                 620

Ser His Pro Ile Gln Trp Asn Ala Pro Gln Pro Ser His Ile Ser Lys
        625                 630                 635                 640

Tyr Ile Leu Arg Trp Arg Pro Lys Asn Ser Val Gly Arg Trp Lys Glu
                        645                 650                 655
```

-continued

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
            770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
            805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
            885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
            930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
            965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln
            1010                1015                1020

Ile Thr Gly Tyr Arg Leu Thr Val Gly Leu Thr Arg Arg Gly Gln
            1025                1030                1035

Pro Arg Gln Tyr Asn Val Gly Pro Ser Val Ser Lys Tyr Pro Leu
            1040                1045                1050

Arg Asn Leu Gln Pro Ala Ser Glu Tyr Thr Val Ser Leu Val Ala
            1055                1060                1065

```
Ile Lys Gly Asn Gln Glu Ser Pro Lys Ala Thr Gly Val Phe Thr
1070            1075                1080

Thr Leu Gln Pro Gly Ser Ser Ile Pro Pro Tyr Asn Thr Glu Val
1085            1090                1095

Thr Glu Thr Thr Ile Val Ile Thr Trp Thr Pro Ala Pro Arg Ile
1100            1105                1110

Gly Phe Lys Leu Gly Val Arg Pro Ser Gln Gly Glu Ala Pro
1115            1120                1125

Arg Glu Val Thr Ser Asp Ser Gly Ser Ile Val Val Ser Gly Leu
1130            1135                1140

Thr Pro Gly Val Glu Tyr Val Tyr Thr Ile Gln Val Leu Arg Asp
1145            1150                1155

Gly Gln Glu Arg Asp Ala Pro Ile Val Asn Lys Val Val Thr Pro
1160            1165                1170

Leu Ser Pro Pro Thr Asn Leu His Leu Glu Ala Asn Pro Asp Thr
1175            1180                1185

Gly Val Leu Thr Val Ser Trp Glu Arg Ser Thr Thr Pro Asp Ile
1190            1195                1200

Thr Gly Tyr Arg Ile Thr Thr Pro Thr Asn Gly Gln Gln Gly
1205            1210                1215

Asn Ser Leu Glu Glu Val Val His Ala Asp Gln Ser Ser Cys Thr
1220            1225                1230

Phe Asp Asn Leu Ser Pro Gly Leu Glu Tyr Asn Val Ser Val Tyr
1235            1240                1245

Thr Val Lys Asp Asp Lys Glu Ser Val Pro Ile Ser Asp Thr Ile
1250            1255                1260

Ile Pro Ala Val Pro Pro Thr Asp Leu Arg Phe Thr Asn Ile
1265            1270                1275

Gly Pro Asp Thr Met Arg Val Thr Trp Ala Pro Pro Pro Ser Ile
1280            1285                1290

Asp Leu Thr Asn Phe Leu Val Arg Tyr Ser Pro Val Lys Asn Glu
1295            1300                1305

Glu Asp Val Ala Glu Leu Ser Ile Ser Pro Ser Asp Asn Ala Val
1310            1315                1320

Val Leu Thr Asn Leu Leu Pro Gly Thr Glu Tyr Val Val Ser Val
1325            1330                1335

Ser Ser Val Tyr Glu Gln His Glu Ser Thr Pro Leu Arg Gly Arg
1340            1345                1350

Gln Lys Thr Gly Leu Asp Ser Pro Thr Gly Ile Asp Phe Ser Asp
1355            1360                1365

Ile Thr Ala Asn Ser Phe Thr Val His Trp Ile Ala Pro Arg Ala
1370            1375                1380

Thr Ile Thr Gly Tyr Arg Ile Arg His His Pro Glu His Phe Ser
1385            1390                1395

Gly Arg Pro Arg Glu Asp Arg Val Pro His Ser Arg Asn Ser Ile
1400            1405                1410

Thr Leu Thr Asn Leu Thr Pro Gly Thr Glu Tyr Val Val Ser Ile
1415            1420                1425

Val Ala Leu Asn Gly Arg Glu Glu Ser Pro Leu Leu Ile Gly Gln
1430            1435                1440

Gln Ser Thr Val Ser Asp Val Pro Arg Asp Leu Glu Val Val Ala
1445            1450                1455

Ala Thr Pro Thr Ser Leu Leu Ile Ser Trp Asp Ala Pro Ala Val
```

```
                1460                1465                1470
Thr Val Arg Tyr Tyr Arg Ile Thr Tyr Gly Glu Thr Gly Gly Asn
    1475                1480                1485
Ser Pro Val Gln Glu Phe Thr Val Pro Gly Ser Lys Ser Thr Ala
    1490                1495                1500
Thr Ile Ser Gly Leu Lys Pro Gly Val Asp Tyr Thr Ile Thr Val
    1505                1510                1515
Tyr Ala Val Thr Gly Arg Gly Asp Ser Pro Ala Ser Ser Lys Pro
    1520                1525                1530
Ile Ser Ile Asn Tyr Arg Thr Glu Ile Asp Lys Pro Ser Gln Met
    1535                1540                1545
Gln Val Thr Asp Val Gln Asp Asn Ser Ile Ser Val Lys Trp Leu
    1550                1555                1560
Pro Ser Ser Ser Pro Val Thr Gly Tyr Arg Val Thr Thr Thr Pro
    1565                1570                1575
Lys Asn Gly Pro Gly Pro Thr Lys Thr Lys Thr Ala Gly Pro Asp
    1580                1585                1590
Gln Thr Glu Met Thr Ile Glu Gly Leu Gln Pro Thr Val Glu Tyr
    1595                1600                1605
Val Val Ser Val Tyr Ala Gln Asn Pro Ser Gly Glu Ser Gln Pro
    1610                1615                1620
Leu Val Gln Thr Ala Val Thr Asn Ile Asp Arg Pro Lys Gly Leu
    1625                1630                1635
Ala Phe Thr Asp Val Asp Val Asp Ser Ile Lys Ile Ala Trp Glu
    1640                1645                1650
Ser Pro Gln Gly Gln Val Ser Arg Tyr Arg Val Thr Tyr Ser Ser
    1655                1660                1665
Pro Glu Asp Gly Ile His Glu Leu Phe Pro Ala Pro Asp Gly Glu
    1670                1675                1680
Glu Asp Thr Ala Glu Leu Gln Gly Leu Arg Pro Gly Ser Glu Tyr
    1685                1690                1695
Thr Val Ser Val Val Ala Leu His Asp Asp Met Glu Ser Gln Pro
    1700                1705                1710
Leu Ile Gly Thr Gln Ser Thr Ala Ile Pro Ala Pro Thr Asp Leu
    1715                1720                1725
Lys Phe Thr Gln Val Thr Pro Thr Ser Leu Ser Ala Gln Trp Thr
    1730                1735                1740
Pro Pro Asn Val Gln Leu Thr Gly Tyr Arg Val Arg Val Thr Pro
    1745                1750                1755
Lys Glu Lys Thr Gly Pro Met Lys Glu Ile Asn Leu Ala Pro Asp
    1760                1765                1770
Ser Ser Ser Val Val Val Ser Gly Leu Met Val Ala Thr Lys Tyr
    1775                1780                1785
Glu Val Ser Val Tyr Ala Leu Lys Asp Thr Leu Thr Ser Arg Pro
    1790                1795                1800
Ala Gln Gly Val Val Thr Thr Leu Glu Asn Val Ser Pro Pro Arg
    1805                1810                1815
Arg Ala Arg Val Thr Asp Ala Thr Glu Thr Thr Ile Thr Ile Ser
    1820                1825                1830
Trp Arg Thr Lys Thr Glu Thr Ile Thr Gly Phe Gln Val Asp Ala
    1835                1840                1845
Val Pro Ala Asn Gly Gln Thr Pro Ile Gln Arg Thr Ile Lys Pro
    1850                1855                1860
```

-continued

```
Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995

Thr Leu Pro His Pro Asn Leu His Gly Pro Glu Ile Leu Asp Val
    2000                2005                2010

Pro Ser Thr Val Gln Lys Thr Pro Phe Val Thr His Pro Gly Tyr
    2015                2020                2025

Asp Thr Gly Asn Gly Ile Gln Leu Pro Gly Thr Ser Gly Gln Gln
    2030                2035                2040

Pro Ser Val Gly Gln Gln Met Ile Phe Glu Glu His Gly Phe Arg
    2045                2050                2055

Arg Thr Thr Pro Pro Thr Thr Ala Thr Pro Ile Arg His Arg Pro
    2060                2065                2070

Arg Pro Tyr Pro Pro Asn Val Gly Gln Glu Ala Leu Ser Gln Thr
    2075                2080                2085

Thr Ile Ser Trp Ala Pro Phe Gln Asp Thr Ser Glu Tyr Ile Ile
    2090                2095                2100

Ser Cys His Pro Val Gly Thr Asp Glu Glu Pro Leu Gln Phe Arg
    2105                2110                2115

Val Pro Gly Thr Ser Thr Ser Ala Thr Leu Thr Gly Leu Thr Arg
    2120                2125                2130

Gly Ala Thr Tyr Asn Ile Ile Val Glu Ala Leu Lys Asp Gln Gln
    2135                2140                2145

Arg His Lys Val Arg Glu Glu Val Val Thr Val Gly Asn Ser Val
    2150                2155                2160

Asn Glu Gly Leu Asn Gln Pro Thr Asp Asp Ser Cys Phe Asp Pro
    2165                2170                2175

Tyr Thr Val Ser His Tyr Ala Val Gly Asp Glu Trp Glu Arg Met
    2180                2185                2190

Ser Glu Ser Gly Phe Lys Leu Leu Cys Gln Cys Leu Gly Phe Gly
    2195                2200                2205

Ser Gly His Phe Arg Cys Asp Ser Ser Arg Trp Cys His Asp Asn
    2210                2215                2220

Gly Val Asn Tyr Lys Ile Gly Glu Lys Trp Asp Arg Gln Gly Glu
    2225                2230                2235

Asn Gly Gln Met Met Ser Cys Thr Cys Leu Gly Asn Gly Lys Gly
    2240                2245                2250
```

```
Glu Phe Lys Cys Asp Pro His Glu Ala Thr Cys Tyr Asp Asp Gly
    2255                2260                2265

Lys Thr Tyr His Val Gly Glu Gln Trp Gln Lys Glu Tyr Leu Gly
    2270                2275                2280

Ala Ile Cys Ser Cys Thr Cys Phe Gly Gly Gln Arg Gly Trp Arg
    2285                2290                2295

Cys Asp Asn Cys Arg Arg Pro Gly Gly Glu Pro Ser Pro Glu Gly
    2300                2305                2310

Thr Thr Gly Gln Ser Tyr Asn Gln Tyr Ser Gln Arg Tyr His Gln
    2315                2320                2325

Arg Thr Asn Thr Asn Val Asn Cys Pro Ile Glu Cys Phe Met Pro
    2330                2335                2340

Leu Asp Val Gln Ala Asp Arg Glu Asp Ser Arg Glu
    2345                2350                2355

<210> SEQ ID NO 10
<211> LENGTH: 107
<212> TYPE: PRT
<213> ORGANISM: Homo sapiens

<400> SEQUENCE: 10

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Val Gly Gln Val Glu
    50                  55                  60

Leu Gly Gly Gly Pro Gly Ala Gly Ser Leu Gln Pro Leu Ala Leu Glu
65                  70                  75                  80

Gly Ser Leu Gln Lys Arg Gly Ile Val Glu Gln Cys Cys Thr Ser Ile
                85                  90                  95

Cys Ser Leu Tyr Gln Leu Glu Asn Tyr Cys Asn
            100                 105

<210> SEQ ID NO 11
<211> LENGTH: 810
<212> TYPE: PRT
<213> ORGANISM: Homo sapiens

<400> SEQUENCE: 11

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
                20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110
```

-continued

```
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
        130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
        195                 200                 205
Trp Asp Ser Gln Ser Pro His Ala His Gly Tyr Ile Pro Ser Lys Phe
210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
        275                 280                 285
Val Thr Val Ser Gly His Thr Cys Gln His Trp Ser Ala Gln Thr Pro
    290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
        355                 360                 365
Glu Leu Thr Pro Val Val Gln Asp Cys Tyr His Gly Asp Gly Gln Ser
    370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asn Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
```

```
            530                 535                 540
Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                    580                 585                 590

Pro Trp Gln Val Ser Leu Arg Thr Arg Phe Gly Met His Phe Cys Gly
            595                 600                 605

Gly Thr Leu Ile Ser Pro Glu Trp Val Leu Thr Ala Ala His Cys Leu
            610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
            690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 12
<211> LENGTH: 212
<212> TYPE: PRT
<213> ORGANISM: Homo sapiens

<400> SEQUENCE: 12

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65              70                  75                  80

Ser Lys Glu Ala Leu Ala Glu Asn Asn Leu Asn Leu Pro Lys Met Ala
                85                  90                  95
```

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
210

<210> SEQ ID NO 13
<211> LENGTH: 269
<212> TYPE: PRT
<213> ORGANISM: Homo sapiens

<400> SEQUENCE: 13

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

```
Gln Asp Ile Thr Asp Phe Thr Met Gln Phe Val Ser Ser
            260                 265
```

<210> SEQ ID NO 14
<211> LENGTH: 770
<212> TYPE: PRT
<213> ORGANISM: Homo sapiens

<400> SEQUENCE: 14

```
Met Ala Gln Trp Asn Gln Leu Gln Gln Leu Asp Thr Arg Tyr Leu Glu
1               5                   10                  15
Gln Leu His Gln Leu Tyr Ser Asp Ser Phe Pro Met Glu Leu Arg Gln
            20                  25                  30
Phe Leu Ala Pro Trp Ile Glu Ser Gln Asp Trp Ala Tyr Ala Ala Ser
        35                  40                  45
Lys Glu Ser His Ala Thr Leu Val Phe His Asn Leu Leu Gly Glu Ile
    50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
        115                 120                 125
Ala Asn His Pro Thr Ala Ala Val Val Thr Glu Lys Gln Gln Met Leu
    130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
        195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
```

```
              355                 360                 365
Asp Lys Asp Ser Gly Asp Val Ala Ala Leu Arg Gly Ser Arg Lys Phe
            370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                    405                 410                 415
Arg Cys Gly Asn Gly Gly Arg Ala Asn Cys Asp Ala Ser Leu Ile Val
                420                 425                 430
Thr Glu Glu Leu His Leu Ile Thr Phe Glu Thr Glu Val Tyr His Gln
            435                 440                 445
Gly Leu Lys Ile Asp Leu Glu Thr His Ser Leu Pro Val Val Ile
        450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                    485                 490                 495
Pro Ile Gly Thr Trp Asp Gln Val Ala Glu Val Leu Ser Trp Gln Phe
                500                 505                 510
Ser Ser Thr Thr Lys Arg Gly Leu Ser Ile Glu Gln Leu Thr Thr Leu
            515                 520                 525
Ala Glu Lys Leu Leu Gly Pro Gly Val Asn Tyr Ser Gly Cys Gln Ile
        530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                    565                 570                 575
Leu Ala Leu Trp Asn Glu Gly Tyr Ile Met Gly Phe Ile Ser Lys Glu
                580                 585                 590
Arg Glu Arg Ala Ile Leu Ser Thr Lys Pro Pro Gly Thr Phe Leu Leu
            595                 600                 605
Arg Phe Ser Glu Ser Ser Lys Glu Gly Gly Val Thr Phe Thr Trp Val
        610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                    645                 650                 655
Tyr Lys Ile Met Asp Ala Thr Asn Ile Leu Val Ser Pro Leu Val Tyr
                660                 665                 670
Leu Tyr Pro Asp Ile Pro Lys Glu Glu Ala Phe Gly Lys Tyr Cys Arg
            675                 680                 685
Pro Glu Ser Gln Glu His Pro Glu Ala Asp Pro Gly Ser Ala Ala Pro
        690                 695                 700
Tyr Leu Lys Thr Lys Phe Ile Cys Val Thr Pro Thr Thr Cys Ser Asn
705                 710                 715                 720
Thr Ile Asp Leu Pro Met Ser Pro Arg Thr Leu Asp Ser Leu Met Gln
                    725                 730                 735
Phe Gly Asn Asn Gly Glu Gly Ala Glu Pro Ser Ala Gly Gly Gln Phe
                740                 745                 750
Glu Ser Leu Thr Phe Asp Met Glu Leu Thr Ser Glu Cys Ala Thr Ser
            755                 760                 765
Pro Met
    770
```

<210> SEQ ID NO 15
<211> LENGTH: 298
<212> TYPE: PRT
<213> ORGANISM: Homo sapiens

<400> SEQUENCE: 15

Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
        35                  40                  45

Ile Arg Glu Ile Ser Leu Leu Lys Glu Leu Asn His Pro Asn Ile Val
    50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
    130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
            180                 185                 190

Phe Ala Glu Met Val Thr Arg Arg Ala Leu Phe Pro Gly Asp Ser Glu
        195                 200                 205

Ile Asp Gln Leu Phe Arg Ile Phe Arg Thr Leu Gly Thr Pro Asp Glu
    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
            260                 265                 270

Lys Arg Ile Ser Ala Lys Ala Ala Leu Ala His Pro Phe Phe Gln Asp
        275                 280                 285

Val Thr Lys Pro Val Pro His Leu Arg Leu
    290                 295

<210> SEQ ID NO 16
<211> LENGTH: 228
<212> TYPE: PRT
<213> ORGANISM: Homo sapiens

<400> SEQUENCE: 16

Leu Ala Gly Pro Leu Arg Ile Val Val Leu Val Val Ser Val Gly Val
1               5                   10                  15

Thr Trp Ile Val Val Ser Ile Leu Leu Gly Gly Pro Gly Ser Gly Phe
            20                  25                  30

```
Pro Arg Ile Gln Gln Leu Phe Thr Ser Pro Glu Ser Ser Val Thr Ala
        35              40              45

Ala Pro Arg Ala Arg Lys Tyr Lys Cys Gly Leu Pro Gln Pro Cys Pro
    50              55              60

Glu Glu His Leu Ala Phe Arg Val Val Ser Gly Ala Ala Asn Val Ile
65              70              75              80

Gly Pro Lys Ile Cys Leu Glu Asp Lys Met Leu Met Ser Ser Val Lys
            85              90              95

Asp Asn Val Gly Arg Gly Leu Asn Ile Ala Leu Val Asn Gly Val Ser
            100             105             110

Gly Glu Leu Ile Glu Ala Arg Ala Phe Asp Met Trp Ala Gly Asp Val
        115             120             125

Asn Asp Leu Leu Lys Phe Ile Arg Pro Leu His Glu Gly Thr Leu Val
    130             135             140

Phe Val Ala Ser Tyr Asp Asp Pro Ala Thr Lys Met Asn Glu Glu Thr
145             150             155             160

Arg Lys Leu Phe Ser Glu Leu Gly Ser Arg Asn Ala Lys Glu Leu Ala
                165             170             175

Phe Arg Asp Ser Trp Val Phe Val Gly Ala Lys Gly Val Gln Asn Lys
            180             185             190

Ser Pro Phe Glu Gln His Val Lys Asn Ser Lys His Ser Asn Lys Tyr
        195             200             205

Glu Gly Trp Pro Glu Ala Leu Glu Met Glu Gly Cys Ile Pro Arg Arg
    210             215             220

Ser Thr Ala Ser
225
```

BIOMARKERS OF LUNG FUNCTION

This application is a continuation of International Application No. PCT/US2011/020151, filed Jan. 4, 2011, which claims the benefit of U.S. Provisional Application No. 61/292,151, filed Jan. 4, 2010, both of which are entitled: "BIOMARKERS OF LUNG FUNCTION", each of which application is herein incorporated by reference in its entirety.

BACKGROUND

Lung disease, including airway diseases that affect lung function, includes asthma, obstructive pulmonary disease, emphysema, pneumonia, tuberculosis, lung cancer, pulmonary fibrosis, sarcoidosis, HIV/AIDS-related lung disease, alpha-1 antitrypsin deficiency, respiratory distress syndrome, bronchopulmonary dysplasia, embolism, and chronic obstructive pulmonary disease (COPD), among others.

COPD is the fourth leading cause of morbidity and mortality in the United States and is expected to rank third as the cause of death worldwide by 2020 (1). Cigarette smoking is widely recognized as a primary causative factor of COPD and accounts for approximately 80-90% of all cases in the United States (2). It has been estimated that up to 25-50% of cigarette smokers may develop CORD, and its prevalence increases with age (1-4).

The pulmonary component of CORD is primarily characterized by chronic airway inflammation and incompletely reversible, usually progressive, airflow obstruction (5, 1). The operational diagnosis of CORD has traditionally been made by spirometry, as a ratio of the forced expiratory volume in one second ($FEV_1$) to the forced vital capacity (FVC) below 70% (1). Pathophysiological mechanisms believed to underlie CORD include an imbalance between proteinase and anti-proteinase activity in the lung, dysregulation of anti-oxidant activity and chronic abnormal inflammatory response to long-term exposure to noxious gases or particles leading to the destruction of the lung alveoli and connective tissue (5, 1). However, CORD is increasingly recognized as a syndrome associated with significant systemic effects which are attributed to low-grade, chronic systemic inflammation (6, 7, 8, 9).

Conventional methods of diagnosing lung disease such as COPD employ diagnostic tests which rely on the presumed correlation of decreased pulmonary function with the presence of lung disease such as COPD, asthma, fibrosis, emphysema and others. Spirometry, which is the most commonly performed lung function test measures the quantity of air that a subject can exhale and the speed with which the air is exhaled. While lung function tests can provide a general assessment of the functional status of a subject's lungs, they do not distinguish between the different types of lung diseases that may be present. Certain lung related diseases cannot be confirmed based on functional tests alone. In addition, such tests assist in the diagnosis of lung disease only when an abnormality in lung function already exists. Functional diagnostic methods at a single time point also do not predict the rate of progression of the disease.

In contrast to functional diagnostic methods, assessment of protein/peptide biomarkers can be used as diagnostic as well as prognostic indicators of the progression (e.g., predicted rate of progression) of a disease. Thus, the identification of proteins, such as those found in plasma, whose abundance and/or structure is altered in individuals with lung disease can be used to diagnose the presence of disease, provide a prognosis for an individual with lung disease (i.e., predicted rate of progression), and provides a better understanding of biological mechanisms underlying a disease.

SUMMARY

Although cigarette smoking is recognized as the most important environmental cause of COPD, the pathophysiological mechanisms underlying cigarette smoking-related lung function decline are not well understood. The present disclosure provides information regarding the mechanisms involved in CORD, particularly cigarette smoking-related COPD, by identifying a number of plasma peptides and proteins and genes encoding plasma proteins that correlate with lung function or decline in lung function. The present disclosure also describes the use of those peptides and proteins or genes encoding such proteins as biomarkers of lung function decline. The present disclosure also provides information regarding the mechanisms underlying lung function or the rate of lung function decline among subjects with COPD, including adult cigarette smokers with COPD. The plasma peptides and proteins have been identified by the utilization of robust plasma proteomic techniques, statistical analysis and biological pathway analysis. The peptides, proteins and genes encoding such proteins may be used as biomarkers in the diagnosis and prognosis of diseases including lung diseases such as COPD.

The plasma peptides and proteins provided in this disclosure were identified by two proteomic investigations (described herein below as Example 1 and Example 2). The first proteomic investigation discussed in this disclosure used offline strong cation exchange (SCX) fractionation of samples with reverse phase liquid chromatography coupled to a mass spectrometer fitted with electrospray ionization (RP-LC-ESI-MS). Following robust statistical analysis (using two approaches) and database searching, 1,758 peptides were identified in plasma samples from cigarette smokers. Thirty of those peptides mapped to 21 unique proteins and were linearly associated with annualized rates of lung function decline over 5 years among smokers with COPD who were characterized as having rapid or slow (or absent) decline and smokers without COPD. A number of the identified peptides are proteolytic fragments of proteins that are involved in the complement or coagulation systems or which have anti-protease or metabolic functions.

The second proteomic investigation involved the examination of the plasma proteomes of middle-aged or older adult smokers with mild to moderate COPD, with $FEV_1$ decline characterized as either rapid or slow (or absent), using a comprehensive high-throughput proteomic approach, and accurate mass and time (AMT) tag technology. Proteomic data were analyzed using three statistical approaches that permitted the rapid and slow decline groups to be differentiated by 55 peptides that map to 33 unique proteins. Twelve of the proteins have known roles in the complement or coagulation cascade and suggest potential mechanistic biomarkers associated with the rate of lung function decline in COPD.

The present disclosure provides in one aspect a method of diagnosing the presence of, or predicting the rate of lung function decline in a subject with lung disease, comprising determining the level of one or more proteins in Table 7, Table 2 or Table 4, or one or more peptide fragments of one or more proteins in Table 7, Table 2 or Table 4, in a biological sample from said subject. In one embodiment, a determination of the level of one or more proteins in Table 7, Table 2 or Table 4, or one or more peptide fragments of one or more proteins in Table 7, Table 2 or Table 4, are used as an indicator of the presence of lung disease in an individual subject and/or its rate of progression. Determinations of the levels of one or more proteins in Table 7, Table 2 or Table 4, or one or more peptide fragments of one or more proteins in Table 7, Table 2 or Table 4, may also be used to assign individuals to one or more subpopulations (e.g., subpopulations of individuals having a higher risk for COPD with rapid progression or slower progression of lung function decline). In another embodiment, the level of expression of one or more genes encoding one or more proteins in Table 7, Table 2 and/or Table 4 may be determined (e.g., by reverse transcription-polymerase chain reaction or real time PCR) in place of determining the level of protein or peptides translated from the gene products.

Determinations of proteins, peptides, or genes may be made relative to a sample from an individual or a population of individuals not having lung disease, or relative to an added external standard or internal standard such as a different protein.

The present disclosure provides in another aspect a method of diagnosis of or prognosis for a subject having, or suspected of having, a disease (e.g., lung disease such as COPD), comprising determining the level of one or more proteins in Table 2 or Table 4, or one or more peptide fragments of one or more proteins in Table 2 or Table 4, in a biological sample from said subject. In one embodiment the disease is selected from the group consisting of, but not limited to, obstructive pulmonary disease, chronic systemic inflammation, emphysema, asthma, pulmonary fibrosis, cystic fibrosis, obstructive lung disease, COPD, and pulmonary inflammatory disorder. In one embodiment, the disease is COPD.

The methods of providing a diagnosis or prognosis provided herein may advantageously employ samples of biological fluids from a variety of sources, including, but not limited to blood, plasma, serum, lymphatic fluid, sputum, saliva, and/or urine for the direct determination of levels of proteins or peptides, or the indirect determination of levels of proteins or peptides through a measurement of the levels of nucleic acids encoding them. In one embodiment the biological fluid is plasma.

The methods of providing a diagnosis or prognosis provided herein may advantageously employ analytical methods of determining protein or peptide levels in biological fluids including, but not limited to, liquid chromatography separation with mass spectroscopic analysis (LC-MS) where the MS techniques include, but are not limited to, multistage mass spectrometric analysis, data dependent scanning, product ion scans, single ion monitoring, single reaction monitoring, and multiple reaction monitoring. Other methods/techniques of determining the level of proteins/peptides present in samples may also be used such as, for example, immunological detection and immunoaffinity techniques (e.g., ELISA, Western blotting, and various forms of immunological sandwich assays).

Also provided herein are compositions comprising two, three, four, five, six, seven or more proteins or peptide fragments that may be employed in methods of providing a diagnosis or prognosis of a subject having, or suspected of having, a disease (e.g., lung disease such as COPD). In one embodiment, the compositions may comprise proteins or fragments of proteins identified in Table 2, Table 4, or combinations thereof.

In other embodiments, the present disclosure provides compositions comprising two, three, four, five, six, seven or more nucleic acids encoding the proteins and/or peptides identified in Table 2 or Table 4, and optionally comprising at least one promoter operatively coupled to at least one of said nucleic acids. In one embodiment such composition may comprise one, two, three, four, five, six, or more oligonucleotides having at least 80-90 percent, 80-95 percent, 85-95 percent, or 95-100 percent nucleic acid sequence identity to a contiguous sequence of 21 or more nucleotides of a nucleic acid sequence encoding the proteins identified in any of Tables 7, 2 or 4 or fragments thereof.

Also provided are a compositions comprising one or more, two or more, three or more, four or more, five or more, or ten or more different antibodies or fragments thereof, wherein said different antibodies, or antigen binding fragments thereof, are specific to two or more different proteins or peptide fragments identified in any of Table 7, Table 2 or Table 4. In some embodiments, the compositions comprise three, four, five, six seven or more different antibodies, or antigen binding fragments thereof, each specific for a different protein or peptide fragment identified in Table 2 or Table 4.

In another embodiment, the compositions described herein are in the form of: an array having two or more proteins or peptide fragments covalently attached to two or more different spatially addressable locations; an array having two or more antibodies or antigen binding fragments thereof covalently attached to two or more different spatially addressable locations; or an array having two or more nucleic acids covalently attached to two or more spatially addressable locations.

DETAILED DESCRIPTION

Figure 1:
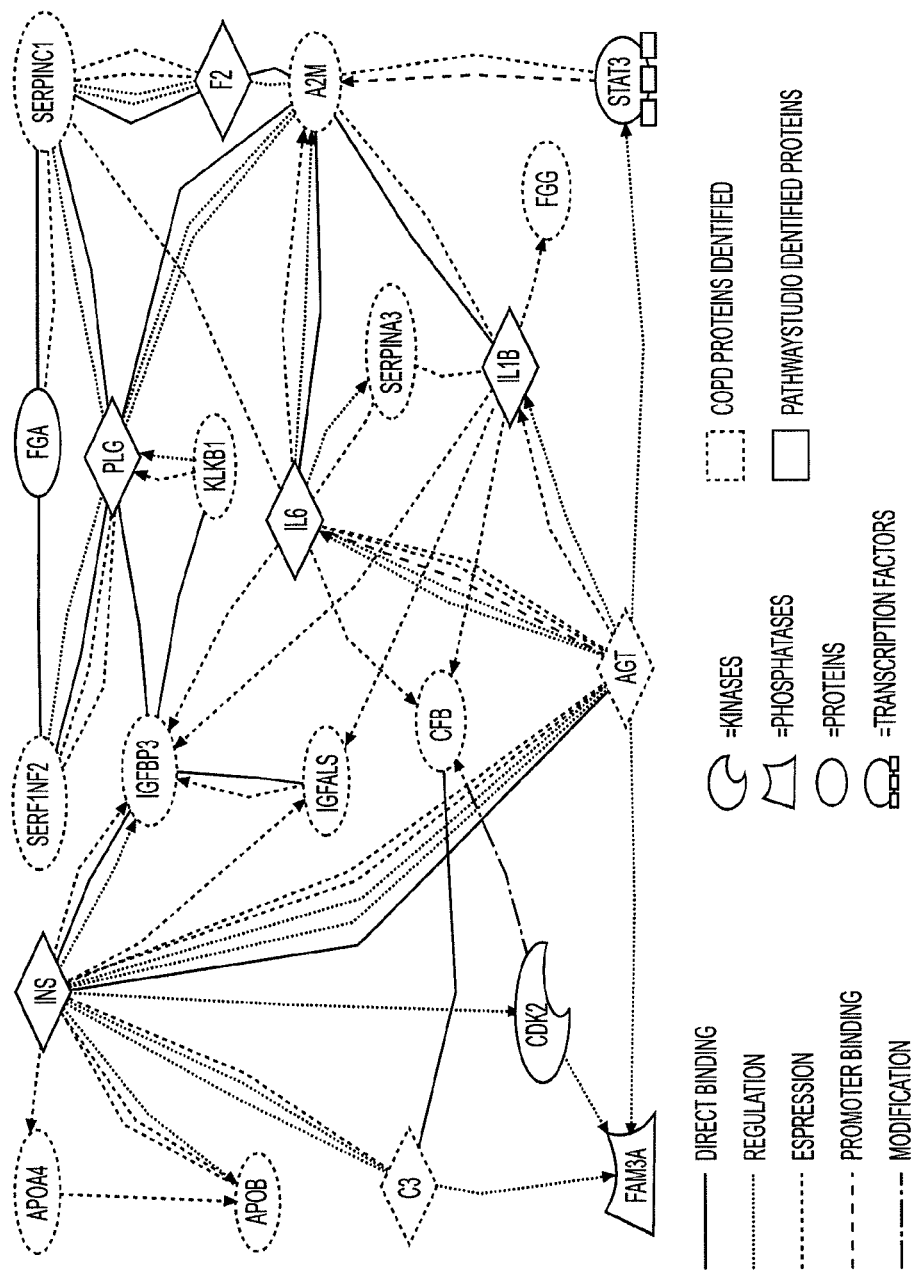
FIG. 1 is a diagram prepared using Pathway Studio™ software by Ariadne Genomics, showing nine proteins having multiple relationships (as determined via natural language processing of published abstracts accessible in pubmed.gov) to 21 of the proteins identified as differentially expressed across the three groups of subjects described in Example 1. The nine proteins identified by Ariadne Genomics' Pathway Studio™ are Insulin 2 (proinsulin) (INS), Plasminogen (PLG), Fibrinogen, alpha polypeptide (FGA), Interleukin 6 (IL6), Coagulation factor II (F2), Interleukin 1 beta (IL1B), Signal transducer and activator of transcription 3 (STAT3), Cyclin dependent kinase 2 (CDK2), and FAM3A (family with sequence similarity 3, member A). Those nine proteins are shown in relation to other proteins identified as differentially expressed.

The present disclosure describes methods of analyzing the protein, peptide, and/or polypeptide content of biosamples to aid in the understanding of molecular mechanisms involved in the development, progression, and/or prognosis of diseases (e.g., lung disease such as COPD) in a subject. Methods are provided for using the abundance of proteins and peptides as biomarkers for diagnostic, prognostic and/or predictive measures of a subject's disease, management of the subject's disease, and/or prediction of the subject's response to clinical treatments for the lung disease. In one embodiment, the disease includes cigarette smoking-related COPD which is assessed by identifying plasma proteins that are differentially expressed and correlate with different rates of decline in lung function ($FEV_1$). Measurements of the abundance of expressed nucleic acids encoding proteins, peptides, and polypeptides may also be used as surrogates for the measurement of these proteins, peptides and polypeptides in the methods described herein.

In addition to providing information such as the name of the protein and the name of the gene encoding the proteins identified herein, the NCBI accession number and version and/or the GI number (aka "gi number") is provided for each protein. The NCBI accession/version numbers and GI numbers uniquely identify nucleic acid and/or protein sequences present in the NCBI database (NCBI, U.S. National Library of Medicine, 800 Rockville Pike, Bethesda, Md., 20894 USA), and are publicly available, for example, on the word wide web at www.ncbi.nlm.nih.gov. Where an NCBI accession number is provided for a precursor protein it is understood that the corresponding mature protein is also available in the NCBI database and considered part of this disclosure unless expressly stated otherwise. In addition, recitation of the protein sequences provided herein indicates that the corresponding gene sequence(s) encoding each protein are also available in the NCBI database at the time of this disclosure and its priority document. Where any accession number does not recite a specific version, the version is taken to be the most recent version of the sequence associated with that accession number at the time the earliest priority document for the present application was filed.

For each proteins recited herein it is understood that the NCBI accession numbers and GI numbers only refer to a sequence that is exemplary of the proteins (and their peptides) encompassed by this disclosure. Unless recited otherwise, the present disclosure includes all isoforms of the proteins identified herein. Isoforms include, but are not limited to: proteins encoded by alternate alleles and haplotypes of the same gene; and/or proteins produced by alternate splicing of transcripts from one or more alleles of the same gene or other forms of alternative processing, including changes due to epigenetic influences. In some embodiments, isoforms include proteins/polypeptides that share greater than 70, 80, 85, 90, 95, 97, 98, or 99% sequence identity over the length of the shorter of the two proteins/polypeptides. In one embodiment, the isoforms of proteins share the amino acid sequence of the peptides recited for the proteins listed in Tables 2, 4 and 7.

In one embodiment an individual or a population of individuals may be considered as not having lung disease or impaired lung function when they do not have clinically relevant signs, symptoms, and/or measures of lung disease. Thus, in various aspects, an individual or a population of individuals may be considered as not having chronic obstructive pulmonary disease, chronic systemic inflammation, emphysema, asthma, pulmonary fibrosis, cystic fibrosis, obstructive lung disease, pulmonary inflammatory disorder, or lung cancer when they do not manifest clinically relevant signs, symptoms and/or measures of those disorders. In another embodiment, an individual or a population of individuals may be considered as not having lung disease or impaired lung function, such as COPD, when they have a $FEV_1/FVC$ ratio greater than or equal to about 0.70 or 0.72 or 0.75. In another embodiment, an individual or population of individuals that may be considered as not having lung disease or impaired lung function are sex- and age-matched with test subjects (e.g., age matched to 5 or 10 year bands) that are current or former cigarette smokers without apparent lung disease who have an $FEV_1/FVC \geq 0.70$ or $\geq 0.75$. Individuals or populations of individuals without lung disease or impaired lung function may be employed to establish the normal range of proteins, peptides or gene expression. Individuals or populations of individuals without lung disease or impaired lung function may also provide samples against which to compare one or more samples taken from a test subject (e.g., samples taken at one or more different first and second times) whose lung disease or lung function status may be unknown. In other embodiments, an individual or a population of individuals may be considered as having lung disease or impaired lung function when they do not meet the criteria of one or more of the above mentioned embodiments.

Identification of Protein(s) and/or Peptide(s) Associated with COPD or its Progression at a Slow or Rapid Rate.

The present disclosure provides in one embodiment a method for identifying protein or peptide biomarkers of a disease that are associated with either the presence of a lung disease, or a slow or a rapid decline in lung function, as measured by a decline in $FEV_1$, in subjects with a lung disease. In one embodiment the lung disease is COPD, which affects the lungs and also the tissues of other organs.

In one embodiment, proteins and/or peptides are identified using expression profiling of samples of a tissue, cells or fluids (e.g., biofluids such as serum, plasma, urine, sputum, saliva, lymph, and the like) from subjects with a lung disease as compared to a profile of peptides in subjects without the disease. In another embodiment, the present disclosure provides polypeptide-based biomarkers that are differentially present in subjects with lung disease versus individuals without lung disease.

In another embodiment, a method for identifying protein and/or peptide biomarkers of a disease that is associated with a decrease in lung function comprises:

a) obtaining an expression profile of proteins and/or peptides in a biological sample from at least one subject (case sample) diagnosed as having a preselected disease that is associated with a decline in lung function (case);

b) obtaining an expression profile of proteins and/or peptides in a biological control sample from at least one subject identified as not having the disease (control);

c) identifying one or more proteins and/or peptides that are differentially expressed in the sample from the subject (case sample) as compared to the control sample; and d) optionally performing a statistical analysis on abundance values of the one or more identified proteins and/or peptides, wherein a statistically significant difference in abundance of the identified peptide(s) and/or protein(s) in the case sample as compared to the control sample identifies the peptide or protein as a biomarker of the preselected disease.

The profiling of proteins and/or peptides may be conducted by any method known in the art including, but not limited to, various mass spectroscopic methods. In some embodiments, proteins/peptides profiles are obtained by liquid chromatography separation of a sample coupled to mass spectroscopic analysis (LC-MS), where the mass spectroscopic analysis techniques including, but are not limited to, multistage mass spectrometric analysis, data dependent scanning, product ion scans, single ion monitoring, single reaction monitoring, and multiple reaction monitoring. Other techniques/instrumentation that may be employed for the analysis of proteins and peptides, include, but are not limited to, FT-ICR MS, LC FT-ICR MS, accurate mass and time (AMT) technology, putative mass and time (PMT) technology, high resolution LC separations and high mass accuracy measurements, MALDI, ESI, offline SCX fractionation with RP-LC-ESI-MS/MS, two-dimensional gel electrophoresis, immunoaffinity methods (e.g., ELISA, Western blotting, in situ immunohistochemistry) and protein array analysis.

In another embodiment, the present disclosure provides a method of using one, two, three, four, five, six seven, eight, ten, fifteen or more different proteins and/or peptides for diagnosing the presence of a lung disease or for developing a prognosis of the rate of lung function decline in a subject.

In another embodiment, the present disclosure provides a method of using one, two, three, four, five, six seven, eight, ten, fifteen or more different proteins and/or peptides for evaluating lung function in the presence of a lung disease or in the absence of a lung disease, or for developing a prognosis of lung function in a subject.

In one aspect, this disclosure also provides methods for comparison of differential protein/peptide expression in one or more subjects with lung disease relative to one or more individuals without lung disease, or in subjects having lung disease such as COPD with little or no decline in lung function, such as by measurement of $FEV_1$, compared with subjects having lung disease such as COPD with rapid decline in lung function. In one embodiment such methods comprise determining the level of one or more proteins that are set forth in Tables 2 and/or 4, or peptide fragments of those proteins or the level of expression of genes encoding those proteins.

This disclosure also provides methods for comparing differential protein expression in subjects with lung disease. Such individuals may be divided into groups having rapid or slow rates of decline in lung function by determining the annualized rate of lung function decline for a subject as the slope of the linear regression of $FEV_1\%$ predicted (i.e., adjusted for age, sex, and height). Subjects with the steepest rate of decline in annualized $FEV_1\%$ predicted (greater than the average annual decline) are considered to have COPD with "rapid decline" (RPD). Those individuals with the least steep or no annualized rate of decline in $FEV_1\%$ predicted (less than the average) are considered to have COPD with slow decline (SLW).

In one embodiment proteins present in a biological sample obtained from one or more cigarette smokers having COPD with rapid decline in lung function may be compared to proteins present in biological samples obtained from cigarette smokers having COPD with slow decline in lung function (SLW), or may be compared to proteins present in biological samples obtained from smokers without COPD or from non-smokers, to identify proteins or peptides differentially expressed in those groups.

Comparison of the differentially expressed proteins identifies potential protein/peptide biomarkers useful for classifying the lung condition or disease (e.g., as slow- or rapid-decline COPD) presented by a subject. Protein/peptide biomarkers may also be identified by analysis of proteins differentially expressed by a subject with a lung disease as compared to proteins expressed by a gender-matched subject without lung disease. Identification of proteins that are differentially abundant among different groups of subjects with lung disease (e.g., age and gender matched subjects) allows an understanding of the mechanisms (e.g., molecular changes) underlying a lung disease and the related decline in lung function. Such proteins are useful as molecular biomarker(s) for diagnosis, determining prognosis, and/or management of a subject's lung disease. For example, the proteins/peptides provided herein can be used for diagnosis and/or prognosis of rate of lung function decline in a subject with a lung disease.

In one embodiment, protein expression among one or more groups of adult cigarette smokers with mild to moderate COPD, but different rates of lung function decline, such as rapid- or slow-decline, may be compared to gender-matched smokers without COPD. Identification of proteins that are differentially abundant among the groups reflects the mechanisms underlying cigarette smoking-related lung function decline. Such proteins/peptides are molecular biomarkers for COPD and are useful in diagnosis, prognosis and/or management of COPD.

In another embodiment a method for identifying protein and/or peptide biomarkers of a disease that is associated with a rapid or slow decrease (decline) in lung function comprises:
   a) obtaining an expression profile of proteins and/or peptides in a biological sample from at least one subject diagnosed as having a preselected disease that is associated with a decline in lung function (case);
   b) obtaining an expression profile of proteins and/or peptides in a biological control sample from at least one subject identified as not having the disease (control);
   c) identifying one or more proteins and/or peptides that are differentially expressed in the case sample as compared to the control sample; and
   d) optionally performing a statistical analysis on abundance values of the one or more identified proteins and/or peptides, wherein a statistically significant difference in abundance of the identified peptide(s) and/or protein(s) in the case sample as compared to the control sample identifies the peptide or protein as a biomarker of the preselected disease.

For the purpose of this disclosure, the term "peptides" includes peptides prepared synthetically, or by any form of proteolysis including, but not limited to, enzymatic proteolysis. Such peptides may be limited to those peptides with a length greater than seven, eight, nine, ten, eleven, twelve, thirteen, fourteen, fifteen, sixteen, seventeen, eighteen, twenty, twenty two, twenty five, thirty, or thirty five amino acids. Such peptides may also be less than 40, 50, 60, 70, 80, or 100 amino acids in length. Alternatively, such peptides may have a range from about 7 to 50, 9-25, 10 to 20, 8 to 24, 9 to 18, 12 to 24, 15 to 45, 18 to 40, 20 to 50, or 25 to 50 amino acids in length.

Methods of Providing a Diagnosis or Prognosis of a Subject Having, or Suspected of Having, a Lung Disease Including COPD Methods are provided for the diagnosis or prognosis of a subject having, or suspected of having, a lung disease, comprising making a determination of one or more proteins in Table 7, or one or more peptides of a protein in Table 7, in a biological sample from a subject. Optionally, the methods comprise making a determination of one or more proteins in Tables 2, 4, 5 and/or 6, or one or more peptides of one or more proteins in Tables 2, 4, 5 and/or 6. In such methods two or more, three or more, four or more, five or more, six or more, eight or more, ten or more, fifteen or more, twenty or more, twenty five or more, thirty or more, or forty or more different proteins or peptides from different proteins in Tables 2, 4, 5 6 and/or 7 may be determined.

Methods are provided for the diagnosis or prognosis of a subject having, or suspected of having a lung disease, comprising determining the level of one or more proteins in Table 7 and/or in Table 2 or Table 4 or one or more peptide fragments of one or more proteins in Table 7 and/or in Table 2 or Table 4, in a biological sample from said subject. In some embodiments the disease is selected from the group consisting of but not limited to obstructive pulmonary disease, chronic systemic inflammation, emphysema, asthma, pulmonary fibrosis, cystic fibrosis, obstructive lung disease, COPD, and pulmonary inflammatory disorder.

Assessment of the level of one or more proteins found in Tables 2 and/or 4, or fragments thereof, provides information for diagnosing lung diseases such as COPD, or for providing a prognosis of lung disease (e.g., COPD progression).

In one embodiment, a method of determining a prognosis of a lung disease can include determining the abundance (quantity or concentration) of one or more biomarkers present in a biological sample obtained from a subject, wherein the one or more biomarkers are selected from the group consisting of: a blood coagulation pathway component (protein), a component of the renin-angiotensin pathway, a complement system protein, a growth factor, a cytokine, a binding protein, a plasma glycoprotein, an anti-inflammatory protein, an immunoglobulin, and a lipoprotein. In another embodiment, a method of determining prognosis of a lung disease can include determining the quantity or concentration of one, two, three, four, five, six, seven, eight, nine, ten, twelve, fifteen, or more proteins listed in Table 7 and/or in Table 2 or Table 4 (or peptides of such proteins) or of transcripts from genes coding for the proteins listed in Table 7 and/or in Table 2 and 4.

In another embodiment, the present disclosure provides a method of managing a subject's lung disease, wherein a therapeutic treatment plan is customized or adjusted based on the status of the disease as determined by assessment of one or more proteins and/or peptide fragments of such proteins identified in Table 7, and/or Tables 2 and/or 4. Exemplary therapeutic treatments for lung disease include administering to the subject, one or more of: immunosuppressants, corticosteroids (e.g. betamethasone delivered by inhaler), b2-adrenergic receptor agonists (e.g., short acting agonists such as albuterol), anticholinergics (e.g., ipratropium, or a salt thereof delivered by nebuliser), and/or oxygen. In addition, where the lung disease is caused by or exacerbated by bacterial or viral infections, one or more antibiotics or antiviral agents may also be administered to the subject. In other embodiments a method of treatment comprises measuring at least one protein or peptide fragment of a protein identified in Table 7, and/or in Tables 2 and/or Table 4, during the course of the subject's lung disease. In such an embodiment, the level of expression of a protein in Table 7, and/or in Table 2 and/or Table 4, may also be assessed by measurement of the nucleic acids (mRNAs) expressed from the gene encoding the protein as surrogate for measuring the protein directly. The course of lung disease may be determined by making a first determination (e.g., taking a first measurement) at a first time, of at least one protein or peptide fragment of a protein identified in Table 7, and/or in Tables 2 and/or Table 4, or mRNA encoding a protein a protein identified in Table 7, and/or in Tables 2 and/or Table 4, in a first sample from the subject; and making a second determination of at least the same protein, peptide fragment or mRNA in a second biological sample obtained from the subject at a second time; and comparing the first determination to the second determination to determine the lung disease is in progression or regression. A method of managing a subject's treatment includes selecting an initial treatment protocol or altering a preselected treatment protocol based on the status or change in the status of the lung disease from the measurements at the first and second times. In other aspects, the method further comprises measuring two, three, four, five, six, seven, eight, ten, twelve, fifteen or more different proteins or peptide fragments of proteins listed in Tables 2 and/or 4, or the level of gene expression (e.g., mRNA levels) for those proteins at one or more times during the management of a subject's lung disease. Any one or more of the proteins identified in Table 5 and/or Table 6, or peptide fragments thereof, may also be employed in such methods of treatment, following the course of lung disease, or managing a subject's treatment.

In another embodiment, the present disclosure provides a method for monitoring the course of progression of a lung disease in a subject comprising: (a) obtaining a first measurement of at least one protein or peptide fragment of a protein listed in Table 7, and/or Table 2 and/or Table 4, or the level of gene expression (e.g., mRNA levels) for that protein in a first biological sample from the subject; (b) obtaining a second measurement of at least the same one protein, peptide fragment or level of gene expression in a second biological sample from the subject, where the second biological sample is obtained from the subject after the first biological sample; and (c) correlating the changes in the first and second measurements with a progression, lack of progression, or regression of lung disease in the subject. Any one or more of the proteins identified in Table 5 and/or Table 6, or peptide fragments thereof, may also be employed in such methods.

Where determinations of one or more proteins or peptide fragments indicate that a treatment administered to a subject is ineffective, the determinations may be taken to indicate that higher levels of an applied therapeutic may be required to effect treatment, the protocol for administration may need to be modified, or that a different therapeutic agent is required. Where determinations of one or more proteins indicate that a treatment administered to a subject is effective, the determinations may be taken to indicate that the course of therapy (e.g., the choice or dosage of therapeutic agent(s) and/or the protocol for administration) should be continued. Where a treatment is only marginally effective based upon the determinations, either a change in the treatment, or an increase in the dosage of a therapeutic agent already being administered to the subject may be indicated.

In embodiments where changes in the levels of the proteins identified in Tables 2, 4 or 7 are observed over time, an increase in at least one protein identified in any of Tables 2, 4 or 7 that is associated with progression of COPD at a slow or rapid rate is indicative of disease progression. In contrast the decrease in at least one protein identified in any of Tables 2, 4 or 7 may be indicative of a lack of disease progression or may be indicative of disease regression. Similarly, an increase in a protein identified in any of Tables 2, 4 or 7 associated with stable COPD is indicative of stability or regression of the disease. Determinations of proteins (e.g., changes in level or amount) may be made by obtaining measurements of the intact protein, peptide fragment(s) of the protein, or nucleic acids (e.g. mRNA) encoding the protein in samples (e.g., first and second samples) obtained from the subject at different times.

Samples for the Identification and Determination of Protein/Peptide Profiles or the Levels of Proteins and/or Peptides Biological sources for detection and determination of the levels of protein/peptide biomarker(s) include any tissue of interest from a subject suspected of having, or diagnosed as having, a disease (e.g., a lung disease such as COPD). In one embodiment, samples for detection of protein(s) and/or peptide(s) of interest include, but are not limited to, serum, plasma, blood, lymphatic fluid, cerebral spinal fluid, sputum or saliva. In another embodiment a protein/peptide biomarker may be detected and levels determined in plasma.

Determination of Protein and Peptide Abundance Levels in Samples

Protein and peptide biomarkers provided herein that are correlated with diseases such as COPD or its progression may be identified without prior knowledge of their identity. For example, a biomarker's amino acid sequence can be determined using peptides present in a sample, peptides from enzymatic digests of a protein containing sample, or peptides derived by sequencing (e.g., sequencing using mass spectroscopy). A sequence for a peptide can be compared to a database of known proteins to identify the proteins from which the peptide was derived.

For the purpose of this disclosure "determination", "determine", or "determining" means measuring or observing the quantity (e.g., mass, weight, or number of moles) of a material or substance or the concentration of a material or substance. Determinations may be made of relative amounts of a material or substance (e.g., the amount of protein in a sample is twice that of the control sample) without ascertaining an absolute amount, provided the determination permits any relevant comparison to be made or method recited herein to be conducted.

Proteins and peptides differentially expressed in subjects having lung diseases such as COPD or in patients with different rates of decline in lung function may be identified and/or their levels measured using a variety of techniques that may be applied to sample protein and/or proteomic analysis. Exemplary methodologies include, but are not limited to, the use of chromatographic separation techniques such as 2-dimensional (2-D) gel electrophoresis, intact protein fractionation, peptide fractionation, and nano-flow liquid chromatography (LC). Analysis of peptides in proteomic studies may employ mass spectrometry (MS), which is a detection technique often used in either matrix assisted laser desorption ionization (MALDI) or electrospray ionization (ESI) for peptide analysis. The MS platforms by which measurements are made include instruments configured as quadrupole, time-of-flight (TOF), ion-trap, and Fourier transform ion cyclotron resonance MS (FTMS) instruments, or hybrid instruments such as triple quadrupole, quadrupole-TOF and ion-trap-FTMS. Recent observations by the Human Proteome Organization's (HUPO) Plasma Proteome Project have shown that offline peptide separation by strong cation exchange (SXC) followed by reverse-phase (RP) LC with ESI-MS/MS can result in the identification of more proteins of low abundance. See Li, et al., 2005 (10), which is hereby incorporated by reference in its entirety. Methods that combine immunological capture and of peptides coupled with mass spectroscopic analysis may also be employed in the methods described herein. See, e.g., U.S. Pat. No. 7,632,686 and U.S. Pat. No. 6,872,575 each of which are incorporated by reference herein.

In one embodiment, determination of a protein and/or peptide present in a biological sample can include its capture on a chromatographic resin that binds the protein and/or peptide. For example, a protein and/or peptide may be captured using a strong or weak cation exchange resin followed by elution. The eluted protein and/or peptide can then be detected by a mass spectrometry method. In another alternative, a protein and/or peptide can be fractionated on an anion exchange resin and detected directly by a mass spectrometry method. In yet another method, a protein and/or peptide can be captured on an immuno-chromatographic resin comprising antibodies that bind the protein and/or peptide followed by a specific detection method or a detection method allowing determination of a protein or peptide level or identification of the protein and/or peptide, such as ELISA or a mass spectrometry method.

Other methods/techniques of isolating, identifying and determining the level of proteins/peptides present in samples include, but are not limited to, SDS-PAGE electrophoresis, two-dimensional gel electrophoresis, intact chromatographic protein fractionation, and peptide chromatographic fractionation, quantitative ligand-binding, and nano-flow liquid chromatography (nano-flow LC).

Nucleic acids encoding proteins and/or peptides may also be measured as surrogates for measurement of the proteins or peptides themselves (e.g., gene expression). In such circumstances a variety of techniques may be employed, including, but not limited to, polymerase chain reaction, nucleic acid array analysis, quantitative RT-PCR (reverse transcriptase PCR), quantitative real time PCR, multiplex PCR, quantitative DNA arrays, quantitative hybridization, chromatography, quantitative rRNA-based amplification, fluorescent probe hybridization, fluorescent nucleic acid sequence specific amplification, loop-mediated isothermal amplification and/or ligase amplification (e.g., ligase chain reaction).

Immunoassays may also be used to identify proteins/peptides that correlate with disease function or for forming a diagnosis or prognosis based on the levels of proteins or peptides present. Such immunoassays include, but are not limited to, ELISA, immunohistochemistry, immunoelectrophoresis, analysis using arrays of immobilized antibodies, and Western blot analysis.

For the purpose of this disclosure antibodies are intended to include all type of antibodies, suitable for use in any given procedure unless specified otherwise. Antibodies include, without limitation, monoclonal antibodies, (monospecific) polyclonal antibodies, Fab(s), Fab'(s), single chain antibodies, diabodies, domain antibodies, miniantibodies, or an antigen binding fragments of any of the foregoing.

In one embodiment, a biological sample may be analyzed by use of an array technology and methods employing arrays such as, for example, a protein or nucleic acid microarray or a biochip bearing an array of proteins (e.g., antibodies) or nucleic acids. A protein array or biochip generally comprises a solid substrate having a generally planar surface, to which a capture reagent is attached. Frequently, the surface of an array or biochip comprises multiple addressable locations, each bearing a bound capture reagent. In one embodiment the arrays permits the detection and/or determination (quantitation) of two, three, four, five, six seven, eight, ten, fifteen or more different biomarkers associated with COPD or its progression at a slow or rapid rate. In another embodiment the array comprises addressable locations for analysis of two, three, four, five, six seven, eight, ten, fifteen or more different proteins or peptide fragment(s) of proteins identified in any of Tables 2, 4 or 7. In another embodiment the array comprises addressable locations for analysis of two, three, four, five, six seven, proteins or fragments of proteins from the group consisting of: a blood coagulation pathway, a component of the renin-angiotensin pathway, and a complement system protein, identified in any of Tables 2, 4 or 7.

Analysis of proteins and/or peptides described herein may be conducted by detection or measurement of individual proteins and/or peptides or a combination of proteins and/or peptides. For example, methods for diagnoses, determining prognosis of a lung disease and/or management of a lung disease in a subject can include use of a composition comprising at least two proteins and/or peptides described herein. Thus, this disclosure includes embodiments or compositions comprising: at least two proteins and/or peptides; one or more nucleic acid sequence, or fragment(s) thereof, encoding proteins and/or peptides; one or more oligonucleotides having at least 80 percent identity to a contiguous sequence of at least 9, 12, 15, 18, 21, 24, 27, or 30 nucleotides of a nucleic acid sequence encoding a protein and/or peptide; or at least two antibodies or fragment(s) thereof specific to a protein or peptide described in any of Tables 2, 4 or 7.

The essential materials and reagents required for diagnosing a lung disease, for determining the prognosis of a lung disease and/or for use in the treatment or management of lung disease in a subject may be assembled together in a kit. The kit generally will comprise components and reagents necessary for determining the level of one or more proteins or peptides (e.g., the proteins or fragments of proteins identified in Tables 2 and/or 4) in a biological sample as well as in control and/or standard samples. For example, a kit may include oligonucleotide sequences, probes, and/or antibodies specific to the one or more of the aforementioned proteins or peptide fragments of those proteins for use in a quantitative assay such as RT-PCR, in situ hybridization, and/or microarray assays.

EXAMPLES

Example 1: Differential Protein Expression Among Two Groups of Adult Cigarette Smokers with Mild to Moderate COPD but Different Rates of Lung Function Decline and a Gender-Matched Group of Smokers without COPD 1.1 Subjects.

Subjects were selected from 244 University of Utah study center participants in the Lung Health Study (LHS) who also participated in the follow-on Genetics of Addiction Project (GAP). LHS enrolled male and female cigarette smokers, aged 35-60 years, with mild or moderate COPD, in a prospective, randomized, multicenter clinical study (11). GAP was a cross-sectional assessment which also enrolled 94 adult cigarette smokers without COPD as a control group. Smoking status was assessed and lung function measured by spirometry at baseline (1986-1989), annually for 5 years, once during 1998-2001 (12), and once in GAP (2003-2004). Spirometry included $FEV_1$ and $FEV_1$ adjusted for age, sex, and height (i.e., as a percentage of predicted) (1). The annualized rate of lung function decline during the 5 years of LHS was calculated for each participant as the slope of the linear regression of $FEV_1$% predicted.

A subset of 54 GAP participants was selected for plasma proteomic analysis in this study: the 18 with the steepest rate of decline in $FEV_1$ (rapid decliners, RPD), the 18 with the least steep or no annualized rate of decline in $FEV_1$ (slow decliners, SLW), and 18 smokers without COPD as a control group. Characteristics of the three groups are shown in Table 1. Over the first 5 years of LHS, the rapid decliners had an average annual decrease in $FEV_1$ of 1.6% predicted/y while the slow decliners had an average increase of 0.8% predicted/y. At the GAP assessment approximately 17 years after baseline, 7/18 (39%) of the RPD participants and 12/18 (67%) of the SLW participants no longer smoked and in the control group, 8/18 (44%) had quit smoking in the three months before GAP participation ($\chi^2$=3.11, 2 d.f., p=0.21).

TABLE 1

Characteristics of study participants.

| | Cigarette Smokers with COPD, Rapid Decline[a] (RPD) (n = 18) | | | Cigarette Smokers with COPD, Slow Decline[a] (SLW) (n = 18) | | | Cigarette Smokers without COPD (n = 18) | |
|---|---|---|---|---|---|---|---|---|
| | Lung Health Study | | | Lung Health Study | | | | |
| Characteristic | Baseline | Year 5 | GAP | Baseline | Year 5 | GAP | GAP | p-value |
| Male, n (%) | | | 13 (72.2) | | | 10 (55.6) | 9 (50.0) | 0.369[b] |
| Age, mean (SD) | | | 64.8 (5.4) | | | 63.6 (7.3) | 57.2 (7.7) | 0.002[c] |
| Cigarettes per Day, mean (SD)[e] | 37.3 (17.2) | 21.6 (19.0) | 16.0 (17.0) | 27.7 (10.7) | 8.3 (11.4) | 5.6 (9.5) | 9.7 (12.0) | 0.167[c] |
| Years Smoked, mean (SD) | | | 42.1 (6.8) | | | 34.8 (9.2) | 30.1 (11.3) | <0.001[c] |
| $FEV_1$ (L), mean (SD) | 2.75 (0.59) | 2.34 (0.67) | 1.70 (0.60) | 2.61 (0.57) | 2.63 (0.66) | 2.32 (0.55) | 3.20 (0.63) | |
| Δ $FEV_1$ (L), mean (SD) | | -0.40 (0.23) | | | 0.02 (0.21) | | na | <0.001[d] |
| $FEV_1$ % predicted, mean (SD) | 76.1 (9.7) | 67.8 (13.3) | 54.6 (16.6) | 74.8 (9.7) | 78.5 (12.1) | 77.2 (14.2) | 103.1 (18.4) | |
| Δ $FEV_1$ % predicted, mean (SD) | | -8.22 (7.34) | | | 3.77 (5.73) | | na | <0.001[d] |

GAP, Genetics of Addiction Project, an average of 17 years after Baseline at which time plasma proteomic analysis was performed; na, not applicable.
[a]Decline in lung function was assessed as the slope of a linear regression of the annualized rate of decline during the first 5 years of participation in the Lung Health Study in $FEV_1$ % predicted (i.e., adjusted for age, height, and gender)
[b]$\chi^2$ = 1.99, 2 d.f. test
[c]Test of association between characteristic and lung function at GAP by linear regression
[d]Change in characteristic from Baseline to Year 5 for RPD versus SLW
[e]At the GAP time point, 7/18 (39%) of RPD, 12/18 (67%) of SLW, and 8/18 (44%) of Control subjects had quit smoking; $\chi^2$ = 3.11, 2 d.f., p = 0.21.

1.2 Plasma Sampling and Processing.

Plasma was sampled by venipuncture using a sodium citrated Vacutainer® tube at least two hours after eating. Within ten minutes of collection, blood was centrifuged for 15 minutes at 1500 g and 2-6° C. The topmost plasma was removed and further centrifuged at 1500 g for 15 minutes. Plasma samples were shipped on dry ice, stored at −80° C., and thawed just before analysis.

1.3 Sample Pooling.

In each of the 3 study groups, plasma samples from 6 subjects were pooled to reduce heterogeneity within the group, increase yield of low-abundance peptides, and minimize instrument run time. Therefore, three pools were evaluated for each of the three study groups, for a total of nine plasma sample pools. Samples were selected for each pool by applying a random number generator.

1.4 Depletion of High-Abundance Plasma Proteins.

All pooled plasma samples were depleted of the top 12 most abundant proteins using a Beckman Coulter IgY-12 High Capacity spin column (part #A24618) using the recommended manufacturer's procedure. In short, 20 µL of plasma were added to 480 µL of dilution buffer. The samples were then filtered through 0.22 µm spin filters by centrifugation for 1 minute at 16,000×g. The depletion columns were then centrifuged for 30 seconds at 400×g to dry the beads. The end caps were attached and the diluted plasma samples were added and mixed by inverting the column. The samples were placed on a rotator (end to end) and incubated at room temperature for 30 minutes. Columns were then inverted and the tips were removed. The samples were then placed in collection tubes and centrifuged for 30 seconds at 400×g. and the depleted flow-through was then collected for digestion.

1.5 Protein Digestion (Plasma)

The depleted flow-through was added to a pre-rinsed Microcon YM-3 (3000 Da) molecular weight Cutoff spin cartridge (Millipore), following manufacturer's recommended protocol, and centrifuged at 14,000×g until 100 µL of retentate remained (~30 min.). The retentate was then transferred to a clean microcentrifuge tube and proteins were reduced using 15 µL of 50 mM ammonium bicarbonate (Pierce) and 1.5 µL of 100 mM DL-1,4-dithiothreitol (Acros, Geel, Belgium) and incubation at 95° C. for 5 minutes. After samples cooled, they were alkylated by the addition of 3 µL of 100 mM iodoacetamide (Pierce) and incubation for 20 minutes in the dark at room temperature. 1.5 µL of 100 ng/µL porcine trypsin (Promega, Madison, Wis.) was then added and the samples were incubated at 37° C. for three hours. An additional 1.5 µL of 100 ng/µL trypsin was then added followed by incubation at 37° C. for approximately 16 hours. To ensure sufficient reagent mixing, all samples were vortexed (30 seconds) and centrifuged (2000×g for one minute) following each solution addition. Samples were dried in a vacuum centrifuge at 45° C. Samples were reconstituted with 50 µL of 3% acetonitrile with 0.1% formic acid and vortexed (30 seconds) prior to fractionation.

1.6 Offline Plasma Fractionation.

Offline fractionation of the plasma tryptic digests in each pooled sample into ten fractions was conducted using a GE healthcare MDLC Ettan (Piscataway, N.J.) fitted with a GE FRAC950 fraction collector fitted with a strong cation exchange (SCX) column (Thermo Fisher Scientific Biobasic SCX, 250×2.1 mm). Ion exchange (IXE) solvent A was 20 mmol/L citric acid (Fisher) in 75% HPLC grade water and 25% acetonitrile (Fisher) (3.8 g citric acid in 1 L of 25% acetonitrile) (pH 2.65). IXE solvent B was 20 mmol/L citric acid and 1 mol/L ammonium chloride (Fisher) in 75% HPLC grade water and 25% acetonitrile (3.8 g citric acid and 53 g ammonium chloride dissolved in 1 L 25% acetonitrile, pH 2.65). The fraction collector was conditioned for approximately 20 minutes before each run with 100% IXE solvent A at 200 µL/minute. The tryptic digest plasma samples were reconstituted in 50 µL of IXE solvent A. Run parameters begin with a 40 µL sample injection and 0% IEX solvent B for 10 minutes, ramped to 60% IEX solvent B in 30 minutes, then to 100% IEX solvent B and held for 5 minutes. The system flow rate was 200 µL/minute and fractions were collected each minute in a 96 well plate (200 µL fractions). The fractions were lyophilized at 45° C. and stored at −20° C. until analysis. Samples were re-constituted with 50 µL of 3% acetonitrile with 0.1% formic acid and vortexed (30 seconds) prior to analysis.

1.7 Liquid Chromatography.

All nano-flow capillary liquid chromatography (ncap-LC) analyses were conducted using an Eksigent nanoLC-1D (Monmouth Junction, N.J.) with a Leap technologies (Carrbaro, N.C.) autosampler and a Zorbax 300SB-C8 trap column (5×0.3 mm). Reverse-phase separation was conducted on each of the ten fractions from each pooled sample using a New Objective Picofrit Proteopep™2 (5 cm of C18 packing and a 15 µm tip). The LC run program has a 4 minute trap wash at 10 ul/min, a 10 µL injection volume and a 270 mL/minute flow rate. LC buffer A contains 0.1% formic acid in LCMS grade water (Fisher) and B contains 84% high purity acetonitrile (Fisher) with 0.1% formic acid. The LC gradient starts at 3.5% B and ramped to 9% 13 in 1 minute. The gradient was ramped to 70% B in 37 minutes, 97% B for 12 minutes and then returned to 3.5% B.

1.8 Mass Spectrometry.

All data were collected on a Thermo-Finnagan (San Jose, Calif.) LTQ-FTMS (a hybrid linear ion-trap with a 7 Tesla Fourier transform ion cyclotron resonance MS) with Xcalibur™ 2.0 and fitted with a New Objective Picoview 550 nanospray ionization source. Full scan data were collected at 50,000 resolution (at 400 m/z) with a mass-to-charge ratio (m/z) range of 400 to 2000. The instrument was externally calibrated no less than 5 days prior to acquisition following manufacturer recommended protocol with caffeine, NRFA and Ultramark. All data were collected using data dependent scanning with multistage MS (MS/MS) using collision-induced dissociation (CID) with a 3 m/z isolation width, normalized collision energy of 35, and 30 millisecond activation in the ion-trap MS (unit mass resolution) on the top five most abundant peptides. Charge state screening and monoisotopic precursor selection were enabled. The acquisition has a 30 second dynamic exclusion using an m/z range of 0.01 low to 1.01 high for the exclusion list with an exclusion limit of 500 m/z values.

1.9 Database Searching.

Database searching was conducted using Thermo-Finnagan Bioworks 3.3.1 SP1. The Human Refseq database was used (download November 2007 from the National Center of Biological Information) for all searches. Prior to the SEQUEST search, the Human Refseq database was indexed for Trypsin (KR), monoisotopic mass, fully enzymatic (cleavage at both sides), molecular weight range of 400-10000, 3 missed cleavage sites, and posttranslational modifications of oxidation of the methionines at 15.99492 Da and alkylation of the cysteines at 57.02146 Da. Mass accuracy was set to 20 parts per million. For all fractions of each pool, individual SEQUEST files were combined using the Bioworks Multiconsensus report function. The rigorous SEQUEST search constraints were set with a Delta CN≥0.100 and Xcorr vs. charge state of 1.9 for 1+, 2.2 for 2+, and 3.75 for 3+ as suggested by the Human Proteome Organization (HUPO) (13) and 4.0 for 4+. The number of different peptides allowed for protein identification was set to one. The total peak areas were determined using the Bioworks algorithm PepQuan with parameters set to area, mass tolerance of 0.0100, minimum threshold of 1000, number of smoothing points at 5, and including all proteins. The false discovery rate was estimated to be less than 10%. Briefly, a concatenated target-decoy database was created using the human Refseq database. Results were searched against the concatenated database and false positives were estimated as twice the number of passing decoy fragments. The false discovery rate was determined by dividing the false positives by the sum of the true positives and false positives (74).

1.10 Statistical Analysis.

Plasma pools vary in the distribution of peptide abundance values due to expected variability in the experimental process. To allow for comparisons across pools, the median-centered natural logarithm of peptide abundance (peak area) within each pool was calculated to standardize abundance values. Two approaches were used to handle the large amount of missing data which is typical for MS/MS-based proteomic studies. In the first case, assuming missing data represent abundance values below the detection threshold, data were imputed to a value of one-half the minimum intensity for each pool plus a small amount of random error. In the second case, missing data were not imputed and thus no assumptions were made about the source of missing data, such as technical error or the real absence or low abundance of protein in plasma. To identify peptides correlated linearly with the presence of COPD and an increasing rate of lung function decline, the study groups were coded ordinally (control=1, SLW=2 and RPD=3) and regressed against the standardized peptide abundance values. Peptides were included if observed in at least three of the nine sample pools. The non-imputation method requires peptide presence in each of the three study groups for inclusion. Since the condition of normality of each peptide predictor in the linear regression model cannot be guaranteed, empirically derived p-values by a permutation test with 1,000 iterations were obtained. Multiple testing was corrected for by calculation of the false discovery rate and the corresponding q-values were reported (14, 15, 16, 17).

1.11 Protein Annotation and Pathway Analysis.

Mapping of proteins to curated molecular pathways was conducted on Kyoto Encyclopedia of Genes and Genomes (KEGG, at www.genome.jp/kegg/) (18-20). Pathway analysis was conducted with Ariadane Genomics' Pathway Studio™ software version 5.0 (Ariadne Genomics, Inc., Rockville, Md.). The analysis was manually filtered using the expanded pathway analysis tool and limiting analysis to proteins.

1.12 Outcome

Offline SCX fractionation with RP-LC-ESI-MS/MS and robust database searching resulted in the observation of 1,758 unique peptides across all nine pooled samples. The filtering constraints for the imputation and non-imputation methods resulted in 1,133 and 973 peptides, respectively, for statistical analysis. At an FDR level of 10%, a total of 17 peptides were significantly associated with lung function decline for the imputation method, 20 peptides were significant for the non-imputation method, and 7 of these peptides were identified by both methods (Table 2). The regression coefficient from the linear model, along with the associated q-value for each method where applicable, were also presented in Table 2 for each unique peptide. A negative regression coefficient estimate indicated linearly decreasing peptide abundance levels across the 3 study groups, from controls to SLW to RPD, while a positive estimate indicated a linear increase in peptide abundance levels from controls to RPD.

TABLE 2

Unique peptides differentially expressed across the 3 study groups: smokers without COPD, smokers with COPD with slow FEV$_1$ decline, and smokers with COPD with rapid FEV$_1$ decline. Reported regression coefficient estimates for each peptide were significant at the 10% false discovery rate.

| | | Protein Name | No Imputation | | Imputation | |
|---|---|---|---|---|---|---|
| Peptide sequence | Gene symbol | NCBI GI Number and Accession/Version Number | Regression coefficient[1] | q-value | Regression coefficient[1] | q-value |
| Complement System | | | | | | |
| -.GVFVLNK.- | C3 | complement component C3 gi: 4557385, NP_000055.1 | −0.235 | <0.001 | −3.211 | <0.001 |
| K.KVFLDC*C*NYITELRR.Q | C3 | complement component C3 | 0.575 | <0.001 | na | na |
| R.VVLVAVDK.G | C3 | complement component C3 | −2.323 | <0.001 | na | na |
| K.YFKPGM#PFDLM#VFVTNPDGSPAYR.V | C3 | complement component C3 | −0.863 | 0.094 | −1.397 | <0.001 |
| R.IPIEDGSGEVVLSR.K | C3 | complement component C3 | −2.998 | 0.094 | na | na |
| K.PGFTIVGPNSVQC*YHFGLSPDLPIC*K.E | CFH | complement factor H gi: 4504375, NP_000177.1 | −0.547 | <0.001 | na | na |
| K.SSNLIILEEHLK.N | CFH | complement factor H | −0.705 | 0.059 | na | na |
| K.VKDISEVVTPR.F | CFB | complement factor B gi: 4502397, NP_001701.1 | 0.603 | <0.001 | 0.603 | 0.087 |

TABLE 2-continued

Unique peptides differentially expressed across the 3 study groups: smokers without COPD, smokers with COPD with slow FEV$_1$ decline, and smokers with COPD with rapid FEV$_1$ decline. Reported regression coefficient estimates for each peptide were significant at the 10% false discovery rate.

| Peptide sequence | Gene symbol | Protein Name NCBI GI Number and Accession/Version Number | No Imputation Regression coefficient[1] | q-value | Imputation Regression coefficient[1] | q-value |
|---|---|---|---|---|---|---|
| R.RPASPISTIQPK.A | C8G | complement component 8, gamma polypeptide gi: 109731764, AAI13627.1 | 0.801 | <0.001 | na | na |
| R.VPANLENVGFEVQTAED DLKTDFYK.D | C6 | complement component 6 gi: 4559406, NP_000056.1 | na | na | −2.450 | <0.001 |
| R.HLVPGAPFLLQALVR.E | C4A | complement component 4A (Rodgers blood group) gi: 14577919, NP_009224.1 | na | na | −3.720 | 0.087 |
| R.LLEPHC*FPLSLVPTEFC* PSPPALK.D | C7 | complement component 7 gi: 45580688, NP_000578.2 | na | na | −2.111 | 0.087 |
| *Coagulation System* | | | | | | |
| R.LTIGEGQQHHLGGAK.Q | FGG | fibrinogen gamma chain gi: 4503715, NP_000500.1 | 1.145 | 0.059 | na | na |
| K.EKGEIQNILQK.V | KLKB1 | kallikrein B, plasma (Fletcher factor) 1 gi: 4504877, NP_000883.1 | 2.543 | <0.001 | na | na |
| K.FEVQVTVPK.I | A2M | alpha 2 macroglobulin gi: 4557225, NP_000005.1 | −0.329 | <0.001 | na | na |
| R.KAAISGENAGLVR.A | ITIH1 | inter-alpha (globulin) inhibitor H1 gi: 4504781, NP_002206.1 | 0.272 | <0.001 | na | na |
| K.GFPIKEDFLEQSEQLF GAKPVSLTGK.Q | SERPINF2 | serpin peptidase inhibitor, clade F (alpha-2 antiplasmin, pigment epithelium derived factor), member 2 gi: 260064050, NP_001159393 | na | na | −2.183 | 0.087 |
| K.TSDQIHFFFAK.L | SERPINC1 | serpin peptidase inhibitor, clade C (antithrombin), member 1 gi: 4502261, NP_000479.1 | na | na | −4.296 | 0.087 |
| *Anti-protease* | | | | | | |
| R.NLAVSQVVHK.A | SERPINA3 | serpin peptidase inhibitor, clade A (alpha-1 antiproteinase, antitrypsin), member 3 gi: 4501843, NP_001076.1 | −0.226 | <0.001 | na | na |
| K.VLSALQAVQGLLVAQGR.A | AGT | Angiotensinogen gi: 4557287, NP_000020.1 | −1.132 | <0.001 | −1.132 | <0.001 |
| K.DPTFIPAPIQAKT | AGT | Angiotensinogen | −0.319 | <0.059 | na | na |
| *Metabolic* | | | | | | |
| R.EYSGTIASEANTYLNSK.S | APOB | apo-B100 precursor gi: 105990532, NP_000375.2 | 0.771 | 0.059 | na | na |
| K.DKDQEVLLQTFLDDASP GDKR.L | APOB | apo-B100 precursor | na | na | −2.169 | <0.001 |
| R.ILGEELGFASLHDLQLL GK.L | APOB | apo-B100 precursor | na | na | −2.646 | 0.087 |
| K.KLVPFATELHER.L | APOA4 | apolipoprotein A-IV gi: 4502151, NP000473.1 | −0.458 | <0.001 | −0.458 | <0.001 |
| K.FLNVLSPR.G | IGFBP3 | insulin-like growth factor binding protein 3 gi: 114319031, AB163364.1 | na | na | −3.154 | <0.001 |

TABLE 2-continued

Unique peptides differentially expressed across the 3 study groups: smokers without COPD, smokers with COPD with slow FEV₁ decline, and smokers with COPD with rapid FEV₁ decline. Reported regression coefficient estimates for each peptide were significant at the 10% false discovery rate.

| Peptide sequence | Gene symbol | Protein Name NCBI GI Number and Accession/Version Number | No Imputation Regression coefficient[1] | q-value | Imputation Regression coefficient[1] | q-value |
|---|---|---|---|---|---|---|
| R.VAGLLEDTFPGLLGLR.V | IGFALS | insulin-like growth factor binding protein, acid labile subunit isoform 1 precursor gi: 225579152, NP_001139478.1 | na | na | −2.214 | 0.087 |
| Other | | | | | | |
| R.C*EGPIPDVTFELLR.E | A1BG | alpha-1-B glycoprotein gi: 21071030, NP_570602.2 | −1.037 | 0.059 | −2.196 | <0.001 |
| K.NGVAQEPVHLDSPAIK.H | A1BG | alpha-1-B glycoprotein gi: 21071030, NP_570602.2 | 0.238 | <0.001 | 0.238 | 0.087 |
| K.SEDC*FILDHGK.D | GSN | gelsolin (amyloidosis, Finnish type) gi: 55960302, CAI14416.1 | na | na | −0.303 | 0.087 | na, not applicable. False discovery rate > 10% for this analysis method.
[1]A negative regression coefficient estimate indicates decreasing peptide abundance levels across the 3 study groups, from controls to SLW to RPD, while a positive estimate indicates increasing peptide abundance levels across the 3 study groups.

The 30 unique peptides identified as differentially expressed across the 3 study groups by linear regression mapped to 21 unique proteins. In Table 2 the peptides are grouped according to major function. The majority of the identified peptides (17/30), representing 12 proteins, are involved in the complement cascade which, as part of the innate immune system, promotes host defense mechanisms of bacterial lysis, phagocytosis, and immune cell recruitment and activation (21, 22). Regression analysis across the three study groups indicated a mixed pattern of over- and under-expression among the 17 complement-related peptides.

SERPINA3, or serpin peptidase inhibitor, Clade A (alpha-1 antiproteinase, antitrypsin), member 3, is relatively underexpressed in the RPD group compared with the SLW group, and highest levels are in the control group. SERPINA3 is a protease inhibitor and lower levels of this protein in the RPD support an imbalance in proteases/anti-proteases in the RPD population. Certain allelic variants of SERPINA3 result in reduced protease inhibitor activity and have been associated with COPD (23-25).

Fibrinogen, kallikrein B and inter-alpha (globulin) inhibitor H1, all components of the coagulation system, are relatively over expressed in the COPD groups compared with the control group, with the highest levels in the RPD group. Coagulation is a complex cascade involving plasma proteins and platelets that results in blood clot formation (26). Circulating clotting factors and their proteases and antiproteases regulate this process (27) and the coagulation system is thought to be involved in the thromboembolic complications associated with COPD and smoking (28, 29, 30). Plasma levels of antithrombin (SERPINC1), a component of one of the principal intrinsic anticoagulant systems (31), and alpha-2 antiplasmin, a major regulator of intravascular fibrinolysis (32), are highest in the control group and lowest in the rapid FEV₁ decline COPD group.

Alpha-2 antiplasmin is also involved in the renin-angiotensin system (RAS) as a critical regulator of angiotensin II-mediated vascular remodeling (Huo 2008). Angiotensinogen is an inactive circulating substrate which is converted by renin to angiotensin I, the precursor peptide in the classical RAS cascade (33). The circulating and local tissue renin-angiotensin systems are involved in vascular remodeling (34) and play pivotal pathophysiological roles in hypertension (35) and diabetes (33). Experimental evidence suggests that oxidant stress-induced damage of lung microvascular endothelial cells in cigarette smokers results in endothelial cell apoptosis, capillary loss, impaired angiogenesis, and profound airspace enlargement (29).

Expression of two insulin-like growth factor binding proteins (IGFBP3 and IGFALS) is lowest in the RPD COPD group and highest in the control group. This possibly reflects the lower levels of anabolic hormones, such as insulin-like growth factors and testosterone, found in chronic inflammatory muscle-wasting conditions such as COPD, chronic heart failure, acquired immunodeficiency syndrome, and cancer (36, 37).

Three peptides mapping to apolipoprotein B100 had a mixed pattern of differential expression across the study groups. Apolipoprotein B is the major structural protein of very low- and low-density lipoproteins (VLDL, LDL), and apoB-containing lipoproteins transport cholesterol from the liver and gut to peripheral tissues (38). On the other hand, apolipoprotein A-IV is the major protein component of high-density lipoproteins (HDL) which reverse transport cholesterol from the periphery to the liver for excretion (38) and constitutes a potent endogenous inhibitor of lipid oxidation (39). Apolipoprotein A-IV is relatively underexpressed in the COPD-RPD group compared with the COPD-SLW and control groups.

Gelsolin (GSN) is an actin-binding protein involved in regulating host response to cellular damage in bacterial sepsis (40). Two peptides with opposite directions of differential expression across the study groups mapped to alpha-1B-glycoprotein, a plasma protein of unknown function.

Ariadne Genomics' Pathway Studio™ identified nine other proteins with multiple connections to the 21 proteins identified as differentially expressed across the three groups in this study (FIG. 1). These included insulin (INS, gi:307072, AAA59179.1), plasminogen (PLG, gi:387026, AAA60113.1), fibrinogen alpha (FGA, gi 11761629, NP_068657.1), coagulation factor 2 (F2, gi4503635 NP_000497.1), interleukin 6 (IL6, gi:10834984, NP_000591.1) and interleukin 1 beta (IL1B, gi:386816, AAA74137.1), signal transducer and activator of transcription 3 (STAT3, gi:21618340, NP_644805.1), cyclin dependent kinase 2 (CDK2, gi:30582481, AAP35467.1) and FAM3A (family with sequence similarity 3, member A, gi:57284179, CAI43239.1). Changes in the regulation of plasminogen and its role in coagulation have been associated with smoking and COPD (28). IL6 and IL1B promote the inflammatory response and both have been observed to be increased in the sputum (and IL6 in serum) of smokers and persons with COPD (41, 42, 43, 30).

Furthermore, in a large genome-wide association study, a specific small nucleotide polymorphism found in the IL6 receptor gene is identified as associated with COPD (44). This suggests that IL6 signaling may be an important pathway in COPD. An IL1B gene polymorphism has also been linked with COPD in a Korean population (45). In addition to the human data linking ILB to COPD, a recent mouse model overexpressing IL1B in the lung demonstrated similar tissue changes with inflammation, tissue remodeling and distal airway enlargement (46). Of the 9 additional proteins found by pathway analysis, insulin, plasminogen, interleukin 6 and interleukin 1 beta had the greatest number of interactions with the 21 differentially expressed proteins observed, suggesting that the these additional proteins may represent common mechanistic pathways for COPD in cigarette smokers and for rate of lung function decline in COPD.

1.13 Summary

Using high-resolution MS proteomics and two rigorous statistical methods, multiple peptides were identified whose expression is linearly correlated across three groups of cigarette smokers classified spirometrically as having COPD with slow or no lung function decline, COPD with rapid decline and an unaffected control group. Thirty unique peptides, representing 21 proteins, differentiated the three groups. The majority of the peptides observed are components of the complement or coagulation cascades, consistent with the chronic and abnormal inflammatory response that is the hallmark of COPD and which is often associated with a prothrombotic state (28). Ariadne Genomics' Pathway Studio™ analysis identified nine additional proteins that had multiple interactions with the 21 observed proteins. Interestingly, the four proteins with the greatest number of interactions with the 21 differentially expressed proteins were insulin, plasminogen, interleukin 6, and interleukin 1 beta, all of which have been previously associated with COPD or its complications. Insulin resistance, metabolic syndrome and diabetes have been shown to be associated with COPD (47, 48, 37). Both COPD and metabolic syndrome/insulin resistance appear to be systemic proinflammatory, prothrombotic disorders with significant associated, and often common, comorbidities (47, 36, 48).

There is increasing evidence that the clinical features of COPD correlate poorly with airflow limitation as measured by spirometry (8) and, therefore, that spirometric parameters alone were inadequate as diagnostic and prognostic biomarkers for this complex disease (73). A more comprehensive evaluation using a multidimensional index (BODE) that incorporates body mass index, airflow obstruction, dyspnea, and exercise capacity, has been shown to be more predictive of mortality than $FEV_1$ alone (49).

Although offline peptide fractionation enables the identification of a greater number of low-abundance plasma proteins, offline fractionation adds to the instrument time required for the data collection from each sample. In this study, each pooled sample was fractionated offline into 10 well-separated fractions, thus increasing the data collection time by a factor of 10. In the interest of reasonable data collection times, the 18 plasma samples in each study group were grouped into 3 pools of 6 samples each, for a total of 90 RP-LC-MS/MS samples in the study, each requiring approximately 2 hours per data collection (not including blanks and quality controls collected every 10 samples). A disadvantage of sample pooling is the inability to collect information on individual variation. However, a benefit is the dilution of undesired individual variation (noise), and the amplification of any signal, by the factor of dilution (i.e., 6 in this study).

Example 2: Differential Protein Expression Among Two Groups of Adult Cigarette Smokers with Mild to Moderate COPD but Different Rates of Lung Function Decline The plasma proteomes of 40 adult cigarette smokers with mild to moderate COPD were analyzed. Subjects were clinically characterized as having either rapid decline (RPD, n=20) or slow to no decline (SLW, n=20) in $FEV_1$ over a five-year interval. The accurate mass and time (AMT) tag technology utilized is a comprehensive high-throughput proteomic approach based upon a putative time and mass tag database (PMT), high resolution LC separations and high mass accuracy measurements using FT-ICR MS with a 9.4-tesla magnetic field (50-53). Proteins identified as differentially abundant between the two clinical COPD categories (RPD vs. SLW) are exemplary biomarkers of rate of lung function decline in COPD and are useful for monitoring and/or determining disease progression in a subject 2.1 Subjects Subjects were selected from the 624 participants in the Lung Health Study (LHS) at the University of Utah study center. LHS was a prospective, randomized, multicenter clinical study sponsored by the National Heart, Lung, and Blood Institute (NHLBI) which enrolled male and female otherwise healthy cigarette smokers, aged 35-60 years, with mild or moderate COPD during 1986-1989 (11). Lung function was measured by spirometry at baseline, annually for 5 years, and once during 1998-2001 (12). A subset of 244 participated in the Genetics of Nicotine Addiction Project (GAP) during 2003-2004 in which lung spirometry and smoking status were assessed and a plasma sample for proteomic analysis was obtained.

Lung function was assessed as $FEV_1$ and $FEV_1\%$ predicted (e.g., adjusted for age, sex, and height) (I). The annualized rate of lung function decline during the 5 years of LHS was calculated for each participant as the slope of the linear regression of $FEV_1\%$ predicted. The 20 subjects with the steepest rate of decline in $FEV_1$ (rapid decliners, RPD) and the 20 subjects with the least steep or no annualized rate of decline in $FEV_1$ (slow decliners, SLW) were selected for proteomic analysis. Characteristics of the study groups are shown in Table 3. Over the first 5 years of LHS, the rapid decliners had an average annual decrease in $FEV_1$ of 1.52% predicted/year, while the slow decliners had an average increase of 0.73% predicted/year. At the end of LHS, 5/20 (25%) of the RPD and 9/18 (50%) of the SLW participants no longer smoked. At the GAP assessment approximately 12 years later, 8/20 (40%) of the RPD and 11/18 (61%) of the SLW participants no longer smoked. Two SLW subjects had unacceptably low plasma peptide levels and were excluded from this proteomic analysis.

TABLE 3

Characteristics of study subjects

| Characteristic | RPD | | | SLW | | |
|---|---|---|---|---|---|---|
| | Baseline | Year 5 | GAP | Baseline | Year 5 | GAP |
| No. of subjects | | 20 | | | 18 | |
| Male, % | | 70 | | | 67 | |
| Age, mean (SD) | | | 64.9 (5.1) | | | 64.4 (7.4) |
| Cigarettes per day, mean (SD) | 36.4 (16.6) | 26.5 (13.5) | 15.9 (16.8) | 30.2 (10.7) | 10.6 (13.4) | 7.2 (11.0) |
| Years smoked, mean (SD) | 30.5 (5.2) | — | 43.0 (6.9) | 29.1 (6.5) | — | 35.8 (9.3) |
| $FEV_1(L)$, mean (SD) | 2.7 (0.57) | 2.33 (0.63) | 1.68 (0.59) | 2.73 (0.63) | 2.73 (0.69) | 2.4 (0.65) |
| $\Delta FEV_1$(mL/year), mean (SD)[a] | | −75.0 (47.3) | | | 4.9 (43.7) | |
| $FEV_1$ % predicted, mean (SD) | 75.3 (10.28) | 67.7 (12.89) | 54.6 (16.95) | 75.6 (10.0) | 78.7 (12.18) | 76.6 (14.6) |
| $\Delta FEV_1$ % predicted/year, mean (SD)[b] | | −1.52 | | | 0.73 | |

$FEV_1$, forced expiratory volume in one second; RPD, $FEV_1$ rapid decliner group; SLW, $FEV_1$ slow decliner group; GAP, Genetics of Nicotine Addiction Project, an average of 17 years after baseline
[a]Difference in $FEV_1$ (mL/year) at Year 5 from baseline; for RPD vs. SLW, $p < 0.001$
[b]Difference in $FEV_1$ (% predicted) at Year 5 from baseline; for RPD vs. SLW, $p < 0.001$

2.2 Plasma Sampling, Processing and MS Analysis

Plasma samples were obtained from each subject at least 2 h after eating by venipuncture using a sodium citrated Vacutainer tube (BD, Franklin Lakes, N.J.). Within 10 min of collection, blood was centrifuged at 1500×g for 15 min at 2-6° C. The top-most plasma was removed and centrifuged at 1500×g for an additional 15 min. Plasma samples were shipped on dry ice, stored at −80° C. and thawed just before analysis. The plasma samples were analyzed using a comprehensive high-throughput proteomic approach, the accurate mass and time (AMT) tag technology, to facilitate comprehensive high-throughput proteomic measurements. This technology is based upon a putative mass and time (PMT) tag database, high resolution LC separations and high mass accuracy measurements using FT-ICR MS with a 9.4-tesla magnetic field (50-53). This approach involved pooling a subset of randomly selected plasma samples after depletion of abundant proteins and digestion with trypsin. A standard shotgun proteomic analysis was performed where the pool was then separated by strong cation exchange and analyzed by reversed phase capillary LC (rp-LC) coupled directly with an electrospray IT mass spectrometer using a data-dependent MS/MS mode. The results were then used to populate the PMT database. All samples were then analyzed using a high resolution FT-ICR MS system. The data analysis incorporated both the FT-ICR MS accurate mass measurements of intact proteins and the PMT database. This two-stage approach utilized FT-ICR MS to validate peptide AMTs from the PMTs identified using the conventional MS/MS method. This approach provided greater confidence in peptide identifications as well as the foundation for later measurements without the need for MS/MS resulted in greater sensitivity and increased throughput (50-53). Details of each step were discussed below.

2.2.1 Depletion of Abundant Proteins from Plasma

The 12 most abundant proteins were depleted using GenWay Seppro 12 spin-columns (GenWay Biotech, Inc., San Diego, Calif., now ProteomeLab-IgY-12, Beckman Coulter, Inc., Fullerton, Calif.) following the manufacturer's protocol. The removal of abundant proteins was monitored by SDS-PAGE.

2.2.2 In-Solution Tryptic Digestion of Plasma

TCA-precipitable protein from the depleted plasma samples was denatured by the addition of urea to 8 M, thiourea to 2 M, DTT to 5 mM, and heating to 60° C. for 30 min. The sample was then diluted fourfold with 100 mM ammonium bicarbonate, and calcium chloride was added to 1 mM. Methylated, sequencing-grade trypsin (Promega, Madison, Wis.) was added at a substrate-to-enzyme ratio of 50:1 (mass:mass) and incubated at 37° C. for 15 h. Sample cleanup was achieved using a 1-mL SPE $C_{18}$ column (Supelco, Bellefonte, Pa.). The peptides were eluted from each column with 1 mL methanol and concentrated via Speed Vac. The samples were reconstituted to 10 μg/μL with 25 mM ammonium bicarbonate and frozen at −20° C. until analyzed.

2.2.3 Strong Cation Exchange Separation

From all 40 samples, six randomly selected plasma samples were depleted of abundant proteins, digested with trypsin as described above, and pooled. Strong cation exchange chromatography was performed on the pooled peptide sample utilizing a Synchropak S 300, 100×2 mm chromatographic column (Thermo Hypersil-Keystone, Bellefonte, Pa.). A one-hour gradient was utilized at a flow rate of 200 μL/min with fractions collected every 2 min. The beginning solvent system was 25% acetonitrile and 75% water containing 10 mM ammonium formate at pH 3.0, adjusted with formic acid; the ending solvent system was 25% acetonitrile and 75% water containing 200 mM ammonium formate at pH 8.0. The peptide mixture was resuspended in 25% acetonitrile and 75% water containing 10 mM ammonium formate at pH 3.0 with formic acid prior to injection. Fractions were lyophilized and stored at −20° C. until LC MS/MS analysis.

2.2.4 MS/MS Analysis of Peptides

Peptide samples were analyzed by reversed phase capillary LC (rp-LC) coupled directly with electrospray tandem mass spectrometers (Thermo Finnigan, models LCQ Duo and DecaXP, San Jose, Calif.). Chromatography was performed on a 60-cm, 150-μm id×360-μm od capillary column (Polymicro Technologies, Phoenix, Ariz.) packed with Jupiter $C_{15}$ 5-μm-diameter particles (Phenomenex, Torrence, Calif.). A solvent gradient was used to elute the peptides using 0.1% formic acid in water (solvent A) and 0.1% formic acid in acetonitrile (solvent B). The gradient was linear from 0-5% solvent B in 20 min, followed by 5-70% solvent B in 80 min, and then 70-85% solvent B in 45 min. Solvent flow rate was 1.8 μL/min. The capillary LC system was coupled to a LCQ IT mass spectrometer (Thermo Finnigan, San Jose, Calif.) using an in-house manufactured ESI interface, in which no sheath gas or makeup liquid was used. The temperature of the heated capillary and the electrospray voltage was 200° C. and 3.0 kV, respectively. Samples were analyzed using the data-dependent MS/MS mode over the m/z range of 300-2000. The three most-abundant ions detected in each MS scan were selected for collision-induced dissociation.

2.2.5 Putative Mass and Time (PMT) Tag Database from Plasma Results

The raw LC-IT data from the pooled sample described above and data from previous multidimensional analysis (54) were reanalyzed to populate the PMT database using a PMT quality score of 1.0 [requires a minimum cross-correlation score (Xcorr) of 2] and a discriminate score of 0.5 (52). This database was used to generate the AMT tag results.

2.2.6 FT-ICR Mass Spectrometry

A modified and enhanced Broker Daltonics 9.4-tesla FT-ICR MS (Bruker Daltonics Inc., Billerica, Mass.) was employed for the high-throughput proteomics, as described by Belov et al. (55). Briefly, the FT-ICR mass spectrometer is combined with the capillary LC system and modified for concurrent internal mass calibration and auto-sampling. Tryptic peptides for each individual sample were resuspended in mobile phase A (0.1% TFA) and analyzed separately using RP capillary LC coupled to an LSI interface with a FT-ICR MS, as previously described (52). Analysis of the LC FT-ICR data was performed using in-house software tools that included ICR-2LS (Pacific Northwest National Laboratory, http://omics.pnl.gov/software/ICR2LS.php). The initial analysis of raw LC FT-ICR data involved a mass transformation or de-isotoping step using ICR-2LS. To generate relative abundances for the peptides, each sample was analyzed by FT-ICR in duplicate.

2.3 Database Searching

The SEQUEST algorithm (56) was run on each of the datasets against the human protein database from the National Center for Biotechnology Information (RefSeq release 10, March 2005). All data were collected using the multidimensional protein identification technology (MudPIT) approach developed by Yates and coworkers (57, 58). Briefly, all accepted SEQUEST results have a delta Cn of 0.1 or greater. Peptides with a +1 charge state were accepted if they were fully tryptic and have a Xcorr of at least 1.9. Peptides with a +2 charge state were accepted if they were fully tryptic or partially tryptic and have an Xcorr of at least 2.2. Peptides with +2 or +3 charge states with an Xcorr of at least 3.0 or 3.75, respectively, were accepted regardless of their tryptic state (58).

2.4 Data Analysis

When peptides were detected in some samples but not others, the undetected peptides were considered to be missing. On average, 60% of data (e.g., potential peptides) were missing across all quantitative MS runs. Missing values could be due, in part or in combination, to several sources, including true absence of the peptide in blood plasma, an abundance of peptides at a level below the detection limit of MS, and failure to correctly identify a peptide. Since the source of the missing data was unclear, a single method of handling missing data would not be appropriate for all peptides. Therefore, differences in peptide abundance between RPD and SLW were assessed using three separate statistical methods. In Method 1, missing values represent peptides not observed. In Method 2, missing values were imputed to a value below the detection threshold to account for low abundance peptides. In Method 3, a conservative proxy measure of peptide abundance was calculated that avoids the imputation of data.

Replicates were averaged for Methods 1 and 2. Each run was standardized by the respective median log base 2 intensity value to allow for direct comparisons across all samples. For Method 2, missing data was imputed to a value of one-half the minimum intensity for each run plus a small amount of random error (SD=0.01). For Method 3, peptide abundance was coded as an ordinal variable corresponding to the number of times the peptide was observed in each replicate (e.g., 0, 1, or 2). This proxy coding correlates significantly with the observed quantitative outcome (r=0.45, p-value <0.0001).

Analysis was restricted to peptides present in at least 20% of the samples. Tests for association of peptide abundance using the ordinal variable with RPD-SLW group were carried out using exact logistic regression implemented in the R statistical software program (59). The exact option was used to correct for small cell counts, and parameter estimates were obtained by Markov chain Monte Carlo 100,000 simulations following 1,000 burn-in iterations. For Methods 1 and 2, a two-sided t-test was performed and empirically derived p-values were obtained by 1,000 permutations of the data. The set of empirical p-values were corrected for multiple testing by reporting the false discovery rate (14-17). All statistical analyses were performed using R version 2.5.1 software (http://www.r-project.org).

2.5 Protein Annotation/Function

Mapping of proteins to curated molecular pathways was conducted on the Kyoto Encyclopedia of Genes and Genomes (KEGG, on the world wide web at www.genome.jp/kegg/) (18-20).

2.6 Outcome 2.6.1 Peptide/Protein Identification and Data Processing

A total of 3,549 non-redundant peptides were identified from 80 independent MS runs (2 technical replicates per sample), representing 533 proteins. Overall, the peptide abundance levels from technical replicates were very similar (mean $R^2$=0.964, SD=0.054). The average number of unique peptides detected in all samples was 1,362.46 (SD=414.17). Two samples (4 MS runs) displayed lower-than-acceptable numbers of peptides, and hence were omitted from further statistical analysis.

2.6.2 Peptide-Level Results

Figure 2:
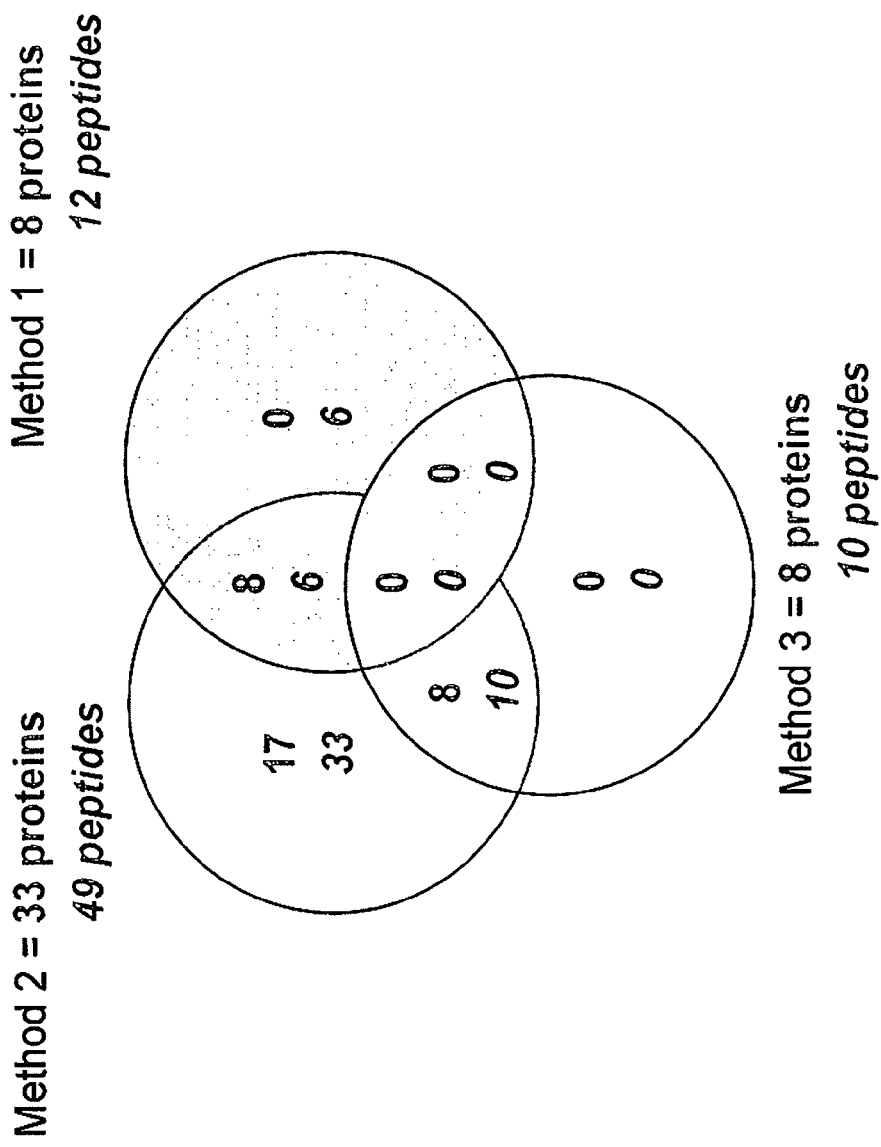
FIG. 2 is a Venn diagram representing an overlap of the peptides (lower number in each pair in italics) and associated non-redundant proteins (upper number in each set not italicized) identified using the three different statistical methods described in Example 2.

Peptide analysis revealed that 12, 49, and 10 peptides were significant at a false discovery rate of 5% for statistical Methods 1, 2, and 3, respectively. FIG. 2 illustrates the overlap on the peptide level among the three statistical methods.

2.6.3 Protein-Level Results

Since each of the statistical methods has its own strengths and weaknesses, the proteomic analysis was conducted on the proteins associated with the non-redundant peptides (Table 4) from all three methods. The 33 proteins associated with the 55 peptides were found by at least one of the three statistical methods and hence were used for subsequent network/pathway analysis. FIG. 2 also illustrates the overlap among the statistical methods on the protein level.

TABLE 4

Fifty-five unique peptides identified from statistical Methods 1, 2, or 3 as differentially expressed between FEV₁ rapid (RPD) and slow (SLW) decliner subjects with chronic obstructive pulmonary disease

| Peptide | NCBI Genbank Accession | Gene symbol | Gene name | Model coefficients[a] | | |
|---|---|---|---|---|---|---|
| | | | | Method 1 | Method 2 | Method 3 |
| GAAANLELIFVGPQHAGNYR | NP_570602.2 | A1BG | alpha 1B-glycoprotein precursor | 0 | -1.50 | 0 |
| LHDNQNGWSGDSAPVELILSDETLPAPEFSPEPESGR | NP_570602.2 | A1BG | alpha 1B-glycoprotein precursor | 0 | 2.67 | 0 |
| VTLTCVAPLSGVDFQLR | NP_570602.2 | A1BG | alpha 1B-glycoprotein precursor | 0 | -2.48 | -2.77 |
| ASVSVLGDILGSAMQNTQN | NP_000005.1 | A2M | alpha-2-macroglobulin precursor | 0 | -2.24 | 0 |
| DSFHLDEQFTVPVEMMQAR | NP_000925.1 | SERPIN F2 | alpha-2-plasmin inhibitor | 1.14 | 1.39 | 0 |
| EATEGKIQEFLSGLPEDTVLLLLNAIHFQGFWR | NP_000925.1 | SERIPIN F2 | alpha-2-plasmin inhibitor | 0 | -3.32 | -1.99 |
| GFPRGDKLFGPDLK | NP_000925.1 | SERPIN F2 | alpha-2-plasmin inhibitor | 0 | -0.88 | 0 |
| AGANVLAKNK | NP_055757.1 | ANKRD6 | ankyrin repeat domain 6 | 0 | 2.37 | 1.81 |
| PYADEFK | NP_000473.1 | APOA4 | apolipoprotein A-IV precursor | 0 | 1.19 | 0 |
| ALYWVNGQVPDGVSK | NP_000375.1 | APOB | apolipoprotein B precursor | 0 | 1.80 | 0 |
| IAELSATAQEIIK | NP_000375.1 | APOB | apolipoprotein B precursor | 0.94 | 0 | 0 |
| LLLQMDSSATAYGSTVSKR | NP_000375.1 | APOB | apolipoprotein B precursor | -1.82 | 0 | 0 |
| KLISVDTEHSNIYLQNGPDR | NP_000087.1 | CP | ceruloplasmin precursor | 0 | 1.80 | 0 |
| MFGNLQGLTMHVGDEVNWYLMGMGNEIDLHTVHFHGHSFQYK | NP_000087.1 | CP | ceruloplasmin precursor | 0 | 2.00 | 0 |
| TLLSNLEEAK | NP_001822.2 | CLU | clusterin isoform 1 | 0 | -0.86 | 0 |
| ETYDFDIAVLR | NP_000495.1 | F10 | coagulation factor X preproprotein | 0 | -1.17 | 0 |
| SSNNPHSPIVEEFQVPYNK | NP_001725.1 | C1S | complement component 1, s subcomponent | 0 | 2.65 | 2.02 |
| AGDFLEANYMNLQR | NP_000055.1 | C3 | complement component 3 precursor | 0.84 | 0.84 | 0 |
| PLSWDIPELVNMGQWK | NP_000055.1 | C3 | complement component 3 precursor | 0 | 1.89 | 0 |
| QKPDGVFQEDAPVIHQEMIGGLR | NP_000055.1 | C3 | complement component 3 precursor | 0 | 2.19 | 0 |
| QLYNVEATSYALLALLQLKDFDFVPPVVR | NP_000055.1 | C3 | complement component 3 precursor | 0 | 2.78 | 0 |
| RQGALELIK | NP_000055.1 | C3 | complement component 3 precursor | -0.63 | 0 | 0 |
| SPYQIHFTK | NP_000055.1 | C3 | complement component 3 precursor | 0 | -1.22 | 0 |
| SYTVAIAGYALAQMGR | NP_000055.1 | C3 | complement component 3 precursor | 0 | 2.41 | 0 |
| NPSDPMPQAPALWIETTAYALLHLLLHEGKAEMADQAAAWLTR | NP_001002029 | C4B | complement component 4B preproprotein | 0 | -2.23 | 0 |

TABLE 4-continued

Fifty-five unique peptides identified from statistical Methods 1, 2, or 3 as differentially expressed between $FEV_1$ rapid (RPD) and slow (SLW) decliner subjects with chronic obstructive pulmonary disease

| Peptide | NCBI Genbank Accession | Gene symbol | Gene name | Model coefficients[a] Method 1 | Method 2 | Method 3 |
|---|---|---|---|---|---|---|
| PGNSDPNMIPDGDFNSYVR | NP_001002029.1 | C4B | complement component 4B preproprotein | 1.13 | 0 | 0 |
| EKFSDASYQSINIPVTQNMVPSSR | NP_001726.1 | C5 | complement component 5 | 0 | 1.41 | 0 |
| FSDASYQSINIPVTQNMVPSSR | NP_001726.1 | C5 | complement component 5 | 0 | 1.55 | 0 |
| AKDLHLSDVFLK | NP_000056.1 | C6 | complement component 6 precursor | 0 | -0.89 | 0 |
| DISEVVTPR | NP_001701.1 | CFB | complement factor B preproprotein | 0 | 3.53 | 2.63 |
| HVIILMTDGLHNMGGDPITVIDEIRDLLYIGK | NP_001701.1 | CFB | complement factor B preproprotein | 0 | 3.73 | 2.39 |
| AVPHPDSQPDTIDHDLLLLQLSEK | NP_001919 | CFD | complement factor D preproprotein | 0 | 1.24 | 0 |
| NDFTWFK | NP_000177.1 | CFH | complement factor H isoform a precursor | 0 | -1.46 | 0 |
| YQIWTTVVDWIHPDLKR | NP_000195.1 | CFI | complement factor 1 preproprotcin | 0 | -1.60 | 0 |
| PNMIDAATLK | NP_000500.1 | FGG | fibrinogen, gamma chain isoform gamma-A | -1.42 | 0 | 0 |
| TYNPDESSKPNMIDAATLK | NP_000500.1 | FGG | fibrinogen, gamma chain isoform gamma-A | 0 | -2.39 | 0 |
| GATYNIIVEALKDQQR | NP_002017 | FN1 | fibronectin 1 isoform 3 preproprotein | 0 | 3.00 | 2.00 |
| TPFVTHPGYDTGNGIQLPGTSGQQPSVGQQMIFEEHGFRR | NP_002017 | FN1 | fibronectin 1 isoform 3 preproprotein | 0 | 2.19 | 1.84 |
| AGALNSNDAFVLK | NP_000168.1 | GSN | gelsolin isoform a precursor | 1.18 | 1.49 | 0 |
| IEGSNKVPVDPATYGQFYGGDSYIILYNYR | NP_000168.1 | GSN | gelsolin isoform a precursor | 1.27 | 1.57 | 0 |
| AAISGENAGLVR | NP_002206.1 | ITIH1 | inter-alpha (globulin) inhibitor H1 | 0 | -3.74 | 0 |
| AHNVVTMR | NP_002208.1 | ITIH3 | inter-alpha (globulin) inhibitor H3 | 0 | -1.53 | 0 |
| ANTVQEATFQMELPK | NP_002209.2 | ITIH4 | inter-alpha (globulin) inhibitor H4 | 0 | 1.99 | 0 |
| RLGVYELLLK | NP_002209.2 | ITIH4 | inter-alpha (globulin) inhibitor H4 | 0 | -2.75 | 0 |
| LWAYLTINQLLAER | NP_002207.1 | ITIH2 | inter-alpha globulin inhibitor H2 polypeptide | 0 | -1.80 | 0 |
| SLPLLMDSV1QALAELEQKVPAAK | NP_443122.2 | PG1.YRP2 | peptidoglycan recognition protein 2 precursor | 0 | -3.53 | -3.41 |
| EIIIHQNYK | NP_000883.1 | KLKB1 | plasma kallikrein B1 precursor | 0 | 3.01 | 0 |
| NNEEYLALIFEKGGSYLGR | NP_002817.2 | QSOX1 | quiescin Q6 sulfhydryl oxidase 1 isoform a | 0 | -1.75 | 0 |
| ELTPEVLQEWLDELEEMMLVVHMPR | NP_000479.1 | SERPINC1 | serine (or cysteine) proteinase inhibitor, clade C (antithrombin), member L antithrombin | 0 | 2.56 | 0 |

TABLE 4-continued

Fifty-five unique peptides identified from statistical Methods 1, 2, or 3 as differentially expressed between FEV$_1$ rapid (RPD) and slow (SLW) decliner subjects with chronic obstructive pulmonary disease

| Peptide | NCBI Genbank Accession | Gene symbol | Gene name | Model coefficients[a] Method 1 | Method 2 | Method 3 |
|---|---|---|---|---|---|---|
| FATTFYQHLADSKNDNDNIFLSPLSISTAFAMTK | NP_000479.1 | SERPIN C1 | serine (or cysteine) proteinase inhibitor, clade C (antithrombin), member L antithrombin | 0 | 3.29 | 0 |
| LYGSEAFATDFQDSAAAK | NP_001076.1 | SERPIN A3 | serpin peptidase inhibitor, clade A, member 3 | 0.88 | 0.88 | 0 |
| NLAVSQVVHK | NP_001076.1 | SERPIN A3 | serpin peptidase inhibitor, clade A, member 3 | −0.59 | 0 | 0 |
| KALQTEMAR | NP_000233.1 | MBL2 | soluble mannose-binding lectin precursor | 0 | −1.51 | 0 |
| GILGKDVSGFSDPYCLLG | NP_954712.1 | UNC13D | unc-13 homolog D | 0 | 0.79 | 2.58 |
| DWHGVPGQVDAAMAGR | NP_000629.2 | VTN | vitronectin precursor | 0.79 | 0.79 | 0 |

[a]Positive coefficient indicates more peptide in RPD vs. SLW; negative coefficient indicates less peptide in RPD vs. SLW; non-zero coefficients were significant at a false discovery rate <5%

Figure 3:
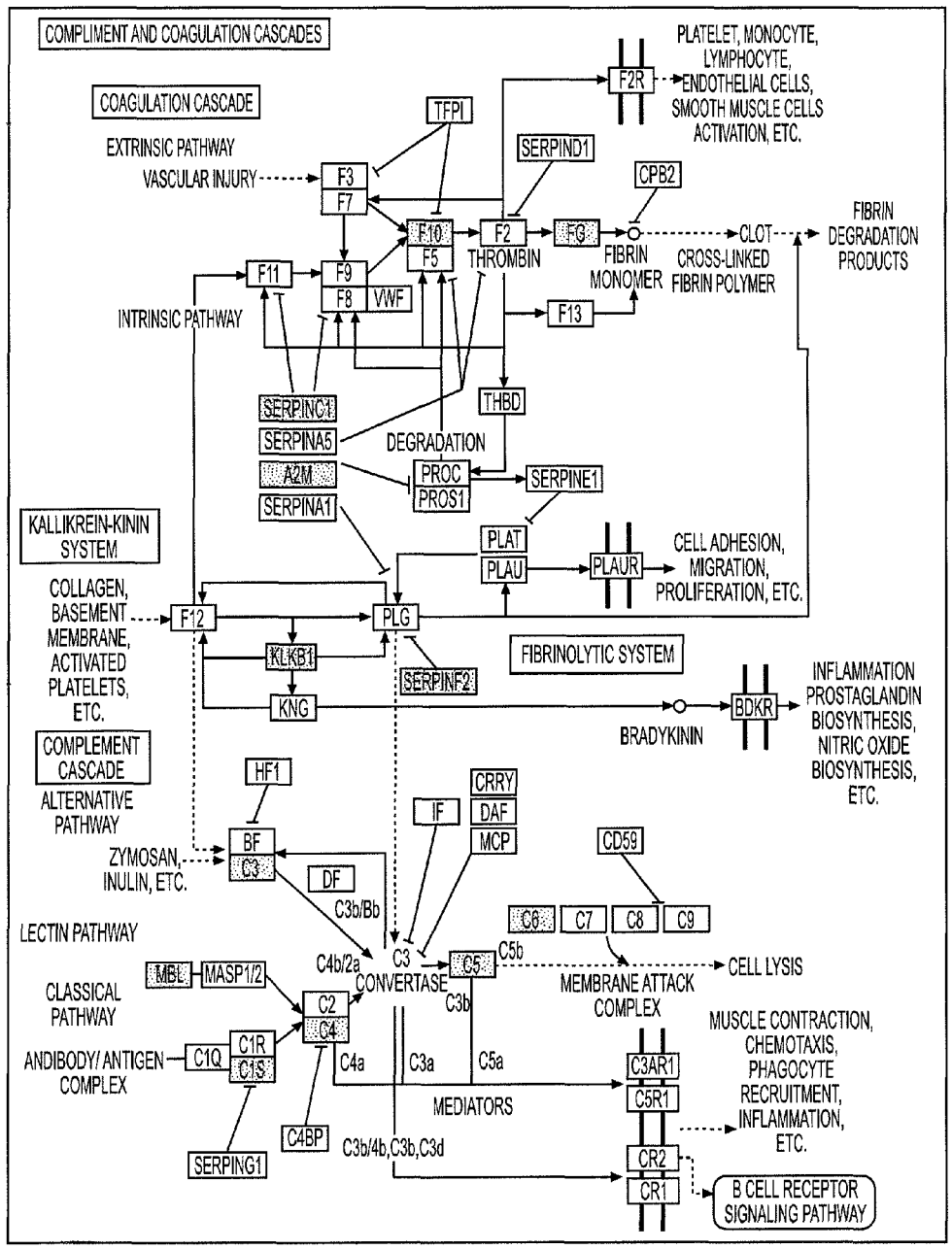
FIG. 3 is a representation of those proteins identified in Example 2 that are known to be part of the coagulation or complement cascade, and their association with other proteins/peptides.

This example used an untargeted global proteomic approach to investigate novel plasma proteins associated with the rate of FEV$_1$ decline in cigarette smokers with COPD. Using three rigorous statistical methods, multiple peptides were found that discriminated between COPD subjects with rapid and slow decline in lung function. The combined analysis identified 55 peptides that putatively correspond to 33 proteins. The majority of these proteins reside in the coagulation and complement cascades, as identified by KEGG (18-20) (FIG. 3). Of these proteins, only serum fibrinogen has been previously linked to an accelerated decline of lung function in COPD subjects (60-62). These proteins represent biomarkers for lung function decline in CORD.

2.6.4 Complement.

The complement system, a complex, multi-protein cascade, is part of the innate immune system and plays an important role in host defenses by promoting bacterial lysis, phagocytosis, and immune cell recruitment and activation (21, 22). In the present example, 12 of the identified proteins are known to be involved in the complement system (FIG. 3). Chronic inflammation and an abnormal inflammatory response to noxious inhaled particles or gases were considered to be key pathogenic mechanisms in COPD (1, 60, 63, 64). Exacerbations of CORD and decline in lung function have been linked to bacterial and viral pulmonary infections (33-35). It is therefore possible that the differential complement activity suggested between the RPD and SLW in this study is the result of an ongoing or recurrent microbial stimulus in the lungs of the rapid decliners, leading to direct complement activation as well as activation secondary to the antibody response to these microbes by the adaptive immune system. A boosted adaptive immune response to viral infections and bacterial colonization of the airways can also result in some subjects with COPD, even after smoking cessation. Molecular mimicry between foreign microbial antigens and self-determinants can result in self-reactivity with autoantibody formation to autoantigens and subsequent complement activation (6, 65). Chronic inflammation in COPD is associated with increased levels of interleukin (IL)-6, which subsequently increases hepatic synthesis of proinflammatory and prothrombotic proteins such as C-reactive protein, fibrinogen and other coagulation factors (4, 66). A recent genetic association study found that the IL-6R locus is associated with COPD (67). IL-6 expression, which is also increased in cigarette smokers (30, 43), has been reported to influence complement 3 and 4 gene expression (68).

In addition to the complement pathway, other proteins were identified that have been shown to play a role in bacterial defenses. Peptidoglycan recognition protein 2 is a bacterial binding protein that is produced by the liver and is part of the non-complement-related innate immune system (69). It may reflect a greater bacterial load in COPD subjects with accelerated lung function decline. Gelsolin is an actin-binding plasma protein that has been reported to be important in regulating the host response to cellular damage that occurs during bacterial sepsis (40). Another identified protein, inter-alpha-inhibitor, plays a role in coagulation during endotoxic shock (70). The identification of these proteins and components of the complement pathway as differentially expressed between rapid and slow FEV$_1$ decliners in COPD suggests that bacterial host defenses may be playing a role in the progression and severity of COPD.

2.6.5 Coagulation

Coagulation involves a complex cascade of plasma protein and platelet activation that results in blood clot formation (26). This process is regulated by circulating clotting factors and their proteases and antiproteases (27). In this study, 12 interleukinoteins that were involved in coagulation were identified as differentially expressed between RPD and SLW (FIG. 3). COPD is associated with higher levels of procoagulant proteins in the blood (71,72). Coagulation may play an important role in COPD progression and has been implicated in the thromboembolic complications associated with COPD and smoking (30, 28, 29). Except for fibrinogen, described above, the proteins identified in the present study differed from those previously reported.

The Use of Additional Protein Biomarkers

The proteins identified in Examples 1 and 2 may be employed with other protein biomarkers of lung function for use in the methods described herein, such as methods of diagnosing lung disease, providing a prognosis to a subject having lung disease, and/or distinguishing individuals with rapid or slow decline in lung function. The proteins identified in Examples 1 and 2 may also be employed with other protein biomarkers of lung function in forming compositions for use conducting the methods described herein. A number of such protein biomarkers have been described. In one embodiment such protein biomarkers include those protein biomarkers capable of use in distinguishing between subjects with rapidly declining pulmonary function and slowly declining pulmonary function. One group of such markers is listed in Table 5a and was described in WO 20081003066 A2, which is hereby incorporated by reference. Those proteins described in WO 20081003066 A2 as having a two-fold or greater difference in abundance between slow decline conditions and rapid decline conditions are listed in Table 5b. In one embodiment, any number of the proteins of either Table 5a or 5b can be employed in the methods described herein with proteins identified in the present study.

TABLE 5a

Proteins Identified in WO20081003066 A2

| NCBI GI and Accession Number/Verison R | Protein Description |
|---|---|
| gi\|4501987\|ref\|NP_001124.1\| | afamin precursor; alpha-albumin [*Homo sapiens*] |
| gi\|4502027\|ref\|NP_000468.1\| | albumin precursor; PRO0883 protein [*Homo sapiens*] |
| gi\|21071030\|ref\|NP_570602.2\| | alpha 1B-glycoprotein [*Homo sapiens*] |
| gi\|4501843\|ref\|NP_001076.1\| | alpha-1-antichymotrypsin, precursor; alpha-1-antichymotrypsin; antichymotrypsin [*Homo sapiens*] |
| gi\|4557225\|ref\|NP_000005.1\| | alpha-2-macroglobulin precursor [*Homo sapiens*] |
| gi\|11386143\|ref\|NP_000925.1\| | alpha-2-plasmin inhibitor; alpha-2-antiplasmin [*Homo sapiens*] |
| gi\|4557287\|ref\|NP_000020.1\| | angiotensinogen precursor; angiotensin II precursor; pre-angiotensinogen; angiotensin I [*Homo sapiens*] |
| gi\|4557321\|ref\|NP000030.1\| | apolipoprotein A-I precursor [*Homo sapiens*] |
| gi\|4502149\|ref\|NP001634.1\| | apolipoprotein A-II precursor [*Homo sapiens*] |
| gi\|4502151\|ref\|NP000473.1\| | apolipoprotein A-IV precursor [*Homo sapiens*] |
| gi\|4502153\|ref\|NP_000375.1\| | apolipoprotein B precursor; apoB-100; apoB-48 [*Homo sapiens*] |
| gi\|4502157\|ref\|NP_001636.1\| | apolipoprotein C-I precursor [*Homo sapiens*] |
| gi\|4557325\|ref\|NP_000032.1\| | apolipoprotein E precursor; apolipoprotein E3 [*Homo sapiens*] |
| gi\|4557327\|ref\|NP_000033.1\| | beta-2-glycoprotein I precursor [*Homo sapiens*] |
| gi\|4557373\|ref\|NP_000051.1\| | biotinidase precursor [*Homo sapiens*] |
| gi\|4502517\|ref\|NP_001729.1\| | carbonic anhydrase I; carbonic dehydratase [*Homo sapiens*] |
| gi\|4503011\|ref\|NP_001299.1\| | carboxypeptidase N, polypeptide 1, 50 kD precursor [*Homo sapiens*] |
| gi\|4557485\|ref\|NP_000087.1\| | ceruloplasmin (ferroxidase); Ceruloplasmin [*Homo sapiens*] |
| gi\|42716297\|ref\|NP_001822.2\| | clusterin isoform 1; complement-associated protein SP-40 [*Homo sapiens*] |
| gi\|4503635\|ref\|NP_000497.1\| | coagulation factor II precursor; prothrombin [*Homo sapiens*] |
| gi\|4503625\|ref\|NP_000495.1\| | coagulation factor X precursor; prothrombinase; factor Xa [*Homo sapiens*] |
| gi\|4557379\|ref\|NP_000053.1\| | complement component 1 inhibitor precursor [*Homo sapiens*] |
| gi\|4502493\|ref\|NP_001724.1\| | complement component 1, r subcomponent [*Homo sapiens*] |
| gi\|7706083\|ref\|NP_057630.1\| | complement component 1, r subcomponent-like precursor; complement C1r-like proteinase; C1r-like serine protease analog [*Homo sapiens*] |
| gi\|4502495\|ref\|NP_001725.1\| | complement component 1, s subcomponent [*Homo sapiens*] |
| gi\|14550407\|ref\|NP_000054.2\| | complement component 2 precursor; C3/C5 convertase [*Homo sapiens*] |
| gi\|4557385\|ref\|NP_000055.1\| | complement component 3 precursor; acylation-stimulating protein cleavage product [*Homo sapiens*] |
| gi\|4502503\|ref\|NP_000706.1\| | complement component 4 binding protein, alpha; Complement component 4-binding protein, alpha polypeptide; complement component 4-binding protein, alpha [*Homo sapiens*] |
| gi\|50345296\|ref\|NP_001002029.1\| | complement component 4B preproprotein; Chido form of C4; basic C4; C4A anaphylatoxin [*Homo sapiens*] |
| gi\|38016947\|ref\|NP_001726.2\| | complement component 5 [*Homo sapiens*] |
| gi\|4559406\|ref\|NP_000056.1\| | Complement component 6 precursor [*Homo sapiens*] |
| gi\|45580688\|ref\|NP_000578.2\| | complement component 7 precursor [*Homo sapiens*] |
| gi\|4557389\|ref\|NP_000553.1\| | complement component 8, alpha polypeptide precursor [*Homo sapiens*] |
| gi\|4502511\|ref\|NP_001728.1\| | complement component 9 [*Homo sapiens*] |
| gi\|4502397\|ref\|NP_001701.1\| | complement factor B preproprotein; C3 proactivator; C3 proaccelerator; glycine-rich beta-glycoprotein; C3/C5 convertase [*Homo sapiens*] |
| gi\|4504375\|ref\|NP_000177.1\| | complement factor H; H factor-1 (complement); factor H-like 1; H factor 2 (complement); H factor 1 (complement) *Homo sapiens*] |
| gi\|11761629\|ref\|NP_068657.1\| | fibrinogen, alpha chain isoform alpha preproprotein [*Homo sapiens*] |
| gi\|11761631\|ref\|NP_005132.1\| | fibrinogen, beta chain preproprotein [*Homo sapiens*] |
| gi\|4503715\|ref\|NP_000500.1\| | fibrinogen, gamma chain isoform gamma-A precursor [*Homo sapiens*] |
| gi\|47132557\|ref\|NP_997647.1\| | fibronectin 1 isoform 1 preproprotein; cold-insoluble globulin; migration-stimulating factor [*Homo sapiens*] |
| gi\|4504165\|ref\|NP_000168.1\| | gelsolin isoform a [*Homo sapiens*] |
| gi\|11321561\|ref\|NP_000604.1\| | hemopexin [*Homo sapiens*] |
| gi\|4504355\|ref\|NP_000176.1\| | heparin cofactor II [*Homo sapiens*] |
| gi\|4504579\|ref\|NP_000195.1\| | I factor (complement) [*Homo sapiens*] |
| gi\|21489959\|ref\|NP_653247.1\| | immunoglobulin J chain [*Homo sapiens*] |
| gi\|4504781\|ref\|NP_002206.1\| | inter-alpha (globulin) inhibitor H1; inter-alpha (globulin) inhibitor, H1 polypeptide [*Homo sapiens*] |
| gi\|4504783\|ref\|NP_002207.1\| | inter-alpha (globulin) inhibitor H2; inter-alpha (globulin) inhibitor, H2 polypeptide [*Homo sapiens*] |

TABLE 5a-continued

Proteins Identified in WO20081003066 A2

| NCBI GI and Accession Number/Verison R | Protein Description |
|---|---|
| gi\|10092579\|ref\|NP_002208.1\| | inter-alpha (globulin) inhibitor H3; Inter-alpha (globulin) inhibitor, H3 polypeptide; pre-alpha (globulin) inhibitor, H3 polypeptide [*Homo sapiens*] |
| gi\|31542984\|ref\|NP_002209.2\| | inter-alpha (globulin) inhibitor H4 (plasma Kallikrein-sensitive glycoprotein); Inter-alpha (globulin) inhibitor, H4 polypeptide; inter-alpha (globulin) inhibitor, H polypeptide-like 1 [*Homo sapiens*] |
| gi\|10835141\|ref\|NP_000563.1\| | interleukin 10 precursor; cytokine synthesis inhibitory factor [*Homo sapiens*] |
| gi\|4504893\|ref\|NP_000884.1\| | kininogen 1; alpha-2-thiol proteinase inhibitor; bradykinin [*Homo sapiens*] |
| gi\|4505047\|ref\|NP_002336.1\| | lumican [*Homo sapiens*] |
| gi\|33188445\|ref\|NP_036222.3\| | microfilament and actin filament cross-linker protein isoform a; actin cross-linking factor; 620 kDa actin binding protein; macrophin 1; trabeculin-alpha; actin cross-linking family protein 7 [*Homo sapiens*] |
| gi\|19923106\|ref\|NP_000437.3\| | paraoxonase 1; Paraoxonase [*Homo sapiens*] |
| gi\|21361845\|ref\|NP_443122.2\| | peptidoglycan recognition protein L precursor [*Homo sapiens*] |
| gi\|4504877\|ref\|NP_000883.1\| | plasma kallikrein B1 precursor; kallikrein 3, plasma; Kallikrein, plasma; kallikrein B plasma; Fletcher factor [*Homo sapiens*] |
| gi\|4505881\|ref\|NP_000292.1\| | plasminogen [*Homo sapiens*] |
| gi\|151465432\|ref\|XP_376519.2\| | PREDICTED: ankyrin repeat domain 6 [*Homo sapiens*] |
| gi\|42662334\|ref\|XP_375941.1\| | PREDICTED: FLJ45139 protein [*Homo sapiens*] |
| gi\|42656986\|ref\|XP_098238.8\| | PREDICTED: SH3 domain protein D19 [*Homo sapiens*] |
| gi\|51464068\|ref\|XP_209550.4\| | PREDICTED: similar to Carboxypeptidase N 83 kDa chain (Carboxypeptidase N regulatory subunit) [*Homo sapiens*] |
| gi\|51458647\|ref\|XP_497680.1\| | PREDICTED: similar to prohibitin [*Homo sapiens*] |
| gi\|51460685\|ref\|XP_497833.1\| | PREDICTED: similar to SULT6B1 [*Homo sapiens*] |
| gi\|4506117\|ref\|NP_000304.1\| | protein S (alpha); Protein S, alpha [*Homo sapiens*] |
| gi\|13325075\|ref\|NP_002817.2\| | quiescin Q6 [*Homo sapiens*] |
| gi\|5803139\|ref\|NP_006735.1\| | RBP4 gene product [*Homo sapiens*] |
| gi\|21361198\|ref\|NP_000286.2\| | serine (or cysteine) proteinase inhibitor, clade A (alpha-1 antiproteinase, antitrypsin), member 1; protease inhibitor 1 (anti-elastase), alpha-1-antitrypsin [*Homo sapiens*] |
| gi\|4507377\|ref\|NP_000345.1\| | serine (or cysteine) proteinase inhibitor, clade A (alpha-1 antiproteinase, antitrypsin), member 7; thyroxine-binding globulin; thyroxin-binding globulin [*Homo sapiens*] |
| gi\|4502261\|ref\|NP_000479.1\| | serine (or cysteine) proteinase inhibitor, clade C (antithrombin), member 1; antithrombin III [*Homo sapiens*] |
| gi\|39725934\|ref\|NP_002606.3\| | serine (or cysteine) proteinase inhibitor, Glade F (alpha-2 antiplasmin, pigment epithelium derived factor), member 1; pigment epithelium-derived factor [*Homo sapiens*] |
| gi\|4502133\|ref\|NP_001630.1\| | serum amyloid P component precursor; penlaxin-related; 9.5S alpha-1-glycoprotein [*Homo sapiens*] |
| gi\|7382460\|ref\|NP_001031.2\| | sex hormone-binding globulin; Sex hormone-binding globulin (androgen binding protein) [*Homo sapiens*] |
| gi\|4557739\|ref\|NP_000233.1\| | soluble mannose-binding lectin precursor; Mannose-binding lectin 2, soluble (opsonic defect); mannose binding protein [*Homo sapiens*] |
| gi\|4507659\|ref\|NP_003283.1\| | translocated promoter region (to activated MET oncogene); Tumor potentiating region (translocated promoter region) [*Homo sapiens*] |
| gi\|46195765\|ref\|NP_954712.1\| | unc-13 homolog D [*Homo sapiens*] |
| gi\|32483410\|ref\|NP_000574.2\| | vitamin D-binding protein precursor; vitamin D-binding alpha-globulin [*Homo sapiens*] |
| gi\|18201911\|ref\|NP_000629.2\| | vitronectin precursor; serum spreading factor; somatomedin B; complement S-protein; epibolin [*Homo sapiens*] |

TABLE 5b

Proteins Identified in WO20081003066 A2 having twofold or greater difference in abundance between slow and rapid decline in lung function

| NCBI GI Reference Number | Protein Description | Anti-Log (Rapid decline conditions vs. Slow decline conditions | Average Rapid decline conditions to Slow decline conditions Ratio | Standard Deviation | Number of Significant Peptides |
|---|---|---|---|---|---|
| 4501843 | Antichymotrypsin | 0.87 | 0.83 | 0.05 | 2 |
| 4557225 | Alpha-2-macroglobulin | 0.88 | 1.05 | 0.48 | 4 |
| 4502153 | Apolipoprotein B | 1.48 | 1.22 | 0.21 | 17 |
| 4557485 | Ceruloplasmin | 0.97 | 0.82 | 0.34 | 5 |
| 4557385 | Complement component 3 | 0.64 | 0.71 | 0.22 | 15 |
| 11761629 | Fibrogen, alpha chain isoform | 1.24 | 1.29 | 0.37 | 6 |
| 11761631 | Fibrogen, beta chain | 1.41 | 1.23 | 0.30 | 5 |
| 4503715 | Fibrogen, gamma chain isoform | 1.21 | 1.24 | 0.50 | 5 |
| 47132557 | Fibronectin 1 isoform 1 | 0.75 | 0.63 | 0.17 | 2 |
| 4504165 | Gelsolin isoform a | 0.76 | 0.85 | 0.30 | 4 |
| 4504893 | Kininogen 1; bradykinin | 1.20 | 1.27 | 0.10 | 2 |

TABLE 5b-continued

Proteins Identified in WO20081003066 A2 having twofold or greater difference in abundance between slow and rapid decline in lung function

| NCBI GI Reference Number | Protein Description | Anti-Log (Rapid decline conditions vs. Slow decline conditions | Average Rapid decline conditions to Slow decline conditions Ratio | Standard Deviation | Number of Significant Peptides |
|---|---|---|---|---|---|
| 4504877 | Plasma kallikrein B1; kallikrein 3, plasma | 0.46 | | | 1 |
| 21361198 | Serine (or cysteine) proteinase inhibitor; alpha-1-antitrypsin | 1.60 | 1.37 | 0.15 | 4 |
| 4502133 | Serum amyloid P component | 1.26 | 1.23 | 0.04 | 2 |
| 32483410 | Vitamin D-binding protein | 0.86 | | | 1 |

Another group of protein biomarkers that are capable of distinguishing between subjects with rapidly declining pulmonary function and slowly declining pulmonary function, are described in WO 2009/114292 A1, and listed in Table 6 parts a-d. In some embodiments, any number of the proteins identified in Table 6, or in any of its separate subsections (6a, 6b, 6c or 6d), may be employed in the methods described herein with any number of the proteins identified in the present study and/or in combination with any number of the proteins identified in Tables 5a or 5b.

TABLE 6(a)

Proteins identified in Signatures as disclosed in WO 20081003066 A2. The listed accession numbers correspond to entries within the National Center for Biotechnology Information (NCBI) database maintained by the National Institutes of Health.

| Protein | Other names | Human polynucleotide accession no. (NCBI) | Human protein accession no. (NCBI) |
|---|---|---|---|
| Apolipoprotein H | Beta-2 glycoprotein I | NM_000042 | NP_000033 |
| CD40 | CD40L receptor | NM_001250 | NP_001241 |
| Haptoglobin | Hp2-alpha | NM_005143 | NP_005134 |
| IL-8 | Interleukin-8 | NM_000584 | NP_000575 |
| MCP-1 | CCL2 | NM_002982 | NP_002973 |
| TNF-RII | TNFRSF1B | NM_001066 | NP_001057 |
| Apolipoprotein CIII | Apoc3 | NM_000040 | NP_000031 |
| GM-CSF | Colony stimulating factor 2 | NM_000758 | NP_000749 |
| IgA | Immunoglobulin type A | BC087841 | AAH87841 |
| MIP-1α | CCL3 | NM_002983 | NP_002974 |
| Tissue factor | Coagulation factor III | NM_001993 | NP_001984 |
| TNF-α | TNF superfamily member 2 | NM_000594 | NP_000585 |
| α1-antitrypsin | Serpin A1 | NM_000295 | NP_000286 |
| CRP | C-reactive protein | NM_000567 | NP_000558 |
| Fibrinogen | FGA | NM_000508 | NP_000499 |
| MDC | CCL22 | NM_002990 | NP_002981 |
| sVCAM-1 | Soluble VCAM-1 | NM_001078 | NP_001069 |
| IL-4 | Interleukin-4 | AF395008 | AAK71324 |

TABLE 6b

Differences in plasma markers between COPD rapid decliners and individuals without lung disease

| Marker | Fold change | p value (FPR) | q value (FDR) |
|---|---|---|---|
| Alpha-1- antitrypsin | 1.11 | 0.0238 | 0.062 |
| Alpha fetoprotein | 1.38 | 0.0498 | 0.094 |
| Apolipoprotein A1 | 1.38 | 0.0020 | 0.017 |
| Apolipoprotein H | 1.15 | 0.0029 | 0.019 |
| Carcinoembryonic antigen | 1.75 | 0.0022 | 0.017 |
| Eotaxin | 2.64 | 0.0007 | 0.008 |
| Factor VII | 1.16 | 0.0448 | 0.091 |
| Fibrinogen | 1.18 | 0.0231 | 0.062 |
| GM-CSF | 1.51 | 0.0061 | 0.026 |
| Haptoglobin | 2.02 | 0.0115 | 0.034 |
| IL-10 | 1.54 | 0.0116 | 0.034 |
| IL-13 | 1.69 | 0.0086 | 0.031 |
| IL-1 alpha | 1.16 | 0.0336 | 0.079 |
| IL-3 | 1.46 | 0.0496 | 0.094 |
| IL-4 | 4.21 | <0.0001 | 0.000 |
| IL-5 | 1.59 | 0.0041 | 0.023 |
| IL-7 | 2.16 | 0.0044 | 0.023 |
| IL-8 | 1.20 | 0.0398 | 0.088 |
| MCP-1 | 1.51 | <0.0001 | 0.001 |
| Serum amyloid P | 1.28 | 0.0049 | 0.023 |
| Tissue factor | 1.19 | 0.0410 | 0.088 |
| TNF-RII | −1.19 | 0.0071 | 0.028 |
| Thrombopoietin | 7.55 | 0.0117 | 0.034 |
| sVCAM-1 | −1.20 | 0.0002 | 0.003 |
| VEGF | 1.18 | 0.0301 | 0.075 |

TABLE 6b-continued

NCBI Accession Numbers and NCBI GI Numbers for the markers appearing in table 6b are as follows.

| Marker | Accession number and GI |
|---|---|
| alpha-I-antitrypsin | AAB59495.1 GI:177831 |
| alpha fetoprotein | AAB58754.1 GI:178236 |
| apolipoprotein A1 | AAD34604.1 GI:4960066 |
| apolipoprotein H | AAA51766.1 GI:178857 |
| Carinoembryonic antigen | CAA44076.1 GI:1877203 |
| Eotaxin | CAB07027.1 GI:2462478 |
| Factor VII | AAA51983.1 GI:180334 |
| Fibrinogen | CAA50740.1 GI:394794 |
| GM-CSF | AAA52578.1 GI:183364 |
| Haptoglobin | AAA88080.1 GI:386783 |
| IL-10 | NP 000563.1 GI:10835141 |
| IL-13 | NP 002179.2 GI:26787978 |
| IL-1 alpha | CAA27448.1 GI:33786 |
| IL-3 | AAC08706.1 GI:3002475 |
| IL-4 | AAH70123.1 GI:47123367 |
| IL-5 | NP 000870.1 GI:4504671 |
| IL-7 | AAH47698.1 GI:29126905 |
| IL-8 | AAH13615.1 GI:15488984 |
| MCP-1 | AAB29926.1 GI:545465 |
| Serum amyloid P | BAA00060.1 GI:220068 |
| Tissue factor | AAA61152.1 GI:339506 |
| TNF-R11 | NP 001057.1 GI:4507577 |
| Thrombopoietin | AAB33390.1 GI:914226 |
| sVCAM-1 | |
| VGEF | CAC19513.2 1:220732299 |

TABLE 6c

Differences in plasma markers between COPD slow decliners and individuals without lung disease

| Marker | Fold change | p value (FPR) | q value (FDR) |
|---|---|---|---|
| Apolipoprotein H | 1.16 | 0.0230 | 0.696 |
| Cancer antigen 19.9 | 2.29 | 0.0078 | 0.563 |
| Eotaxin | 1.68 | 0.0358 | 0.696 |
| VEGF | 1.11 | 0.0545 | 0.696 |

NCBI Accession Numbers and NCBI GI Numbers for the markers appearing in table 6c are as follows.

| Marker | Accession number and GI |
|---|---|
| apolipoprotein H | AAA51766.1 GI:178857 |
| Cancer antigen 19.9 | none found |
| Eotaxin | CAB07027.1 GI:2462478 |
| VEGF | CAC19513.2 GI:220732299 |

TABLE 6d

Differences in plasma markers between COPD rapid and slow decliners.

| Marker | Fold change | p value (FPR) | q value (FDR) |
|---|---|---|---|
| Cancer antigen 19.9 | −1.43 | 0.0355 | 0.300 |
| IgA | −1.57 | 0.0120 | 0.157 |
| IL-4 | 1.27 | 0.0008 | 0.054 |
| IL-5 | 1.48 | 0.0139 | 0.157 |
| Insulin | −5.86 | 0.0165 | 0.160 |
| MCP-1 | 1.44 | 0.0026 | 0.089 |
| MDC | 1.28 | 0.0422 | 0.300 |
| MIP-1 alpha | −1.26 | 0.0468 | 0.300 |
| Tissue factor | 1.32 | 0.0125 | 0.157 |
| sVCAM-1 | −1.31 | 0.0043 | 0.098 |

NCBI AccessionNumbers and NCBI GI Numbers for the markers appearingin table 6d are as follows

| Marker | Accession number and GI |
|---|---|
| Cancer antigen 19.9 | |
| IgA | CAA10818.1 GI:2632187 |
| IL-4 | AAH70123.1 GI:47123367 |
| IL-5 | NP_000870.1 GI:4504671 |
| Insulin | AAA59179.1 GI:307072 |
| MCP-1 | AAB29926.1 GI:545465 |
| MDC | AAB29191.1 GI:455835 |
| MIP-1 alpha | P10147.1 GI:127078 |
| Tissue factor | AAA61152.1 GI:339506 |
| sVCAM-1 | |

Among the protein biomarkers identified herein, a group of protein biomarkers not described in either WO20081003066 A2 or WO 2009/114292 A1 have been identified. Those protein biomarkers, which include insulin, plasminogen, interleukin 6, interleukin 1 beta (IL1 B), signal transducer and activator of transcription 3 (STAT3), cyclin dependent kinase 2 (CDK2) and FAM3A (family with sequence similarity 3, member A) which were identified using Ariadne Genomics' Pathway Studio™, are listed in Table 7.

TABLE 7

| Protein | GI Number and NCBI Accession/Version | SEQ ID NO: |
|---|---|---|
| complement component 4A (Rodgers blood group) | GI:14577919, NP_009224 (Precursor) | 1 |
| serpin peptidase inhibitor, clade A (alpha-1 antiproteinase, antitrypsin), member 3 | GI:4501843, NP_001076.1 | 2 |
| complement component 8, gamma polypeptide | GI:109731764, AAI13627.1 | 3 |
| serpin peptidase inhibitor, clade F (alpha-2 antiplasmin, pigment epithelium), | GI:260064050, NP_001159393 | 4 |
| insulin-like growth factor binding protein 3 | GI:114319033, DQ884398.1 | 5 |
| insulin-like growth factor binding protein, acid labile subunit | GI:4826772, NP_004961.1 | 6 |
| gelsolin (amyloidosis, Finnish type) | GI:119607896, EAW87490.1 | 7 |
| complement factor D | GI:42544239, NP_001919.2 | 8 |
| fibronectin 1 isoform 3 preproprotein | GI:16933542, NP_002017.1 | 9 |
| Insulin | GI:307072, AAA59179.1 | 10 |

TABLE 7-continued

| Protein | GI Number and NCBI Accession/Version | SEQ ID NO: |
|---|---|---|
| plasminogen | GI:387026, AAA60113.1 | 11 |
| Interleukin 6 | GI:10834984, NP_000591.1 | 12 |
| interleukin 1 beta | GI:386816, AAA74137.1 | 13 |
| signal transducer and activator of transcription 3 | GI:21618340, NP_644805.1 | 14 |
| cyclin dependent kinase 2 | GI:30582481, AAP35467.1 | 15 |
| family with sequence similarity 3, member A (FAM3A) | GI:57284179, CAI43239.1 | 16 |

Other substitutions, modifications, changes and omissions may be made in the design, operating conditions and arrangement of the aspects and embodiments described herein without departing from the spirit of the invention as expressed in the appended claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All of the references cited herein, including patents, patent applications, and publications, are hereby incorporated in their entireties by reference.

The scope of the claims below is not restricted to the particular embodiments described above. The examples are described for illustrative purposes and are not intended to limit the methods and compositions of the present disclosure in any manner. Those of skill in the art will recognize a variety of parameters that can be changed or modified to yield the same results.

REFERENCES

1. Rabe, et al. *Am. J. Respir. Crit. Care Med.* 2007, 176, 532-555.
2. Lokke, et al. *Thorax* 2006, 61, 935-939.
3. Lundbäck, et al. *Proc. Am. Thorac. Soc.* 2007, 4, 502-506.
5. Barnes, et al. 2003. *Eur Respir J*, 22(4), 672-688.
6. Agusti, et al. *Thorax* 2003, 58, 832-834.
7. Agusti and Soriano. COPD as a systemic disease. *COPD* 2008, 5, 138.
8. Fabbri, L. M., & Rabe, K. F. (2007). *Lancet*, 370(9589), 797-799.
9. Rahman, et al. 1996. *Am J Respir Crit Care Med*, 154(4 Pt 1), 1055-1060.
10. Li, et al. (2005). *Proteomics*, 5(13), 3423-3441.
11. Anthonisen, et al. *JAMA* 1994, 272, 1497-1505.
12. Anthonisen, et al. *Am. J. Respir. Crit. Care Med.* 2002, 166, 675-679.
13. Anderson, et al. In: Valafar F., Valafar H. (Eds.). *Proceedings of the International Conference on Mathematics and Engineering Techniques in Medicine and Biological Sciences* (METMBS '04), CSREA Press, Las Vegas 2004, pp. 151-156.
14. Benjamini, et al. *J. Royal. Stat. Soc. B* 1995, 57, 289-300.
15. van den Oord, E. *J. Mol. Psychiatry.* 2005, 10, 230-231.
16. Storey, et al. *Methods Mol. Biol.* 2003, 224, 149-157.
17. Storey, et al. *Proc. Natl. Acad. Sci. U.S.A.* 2003, 100, 9440-9445.
18. Kanehisa, et al. *Nucleic Acids Res.* 2008, 36, D480-D484.
19. Kanehisa, et al. *Nucleic Acids Res.* 2006, 34, D354-D357.
20. Kanehisa, et al. *Nucleic Acids Res.* 2000, 28, 27-30.
21. Bolger, et al. *Am. J. Physiol. Lung Cell. Mol. Physiol.* 2007, 292, L748-L759.
22. Markiewski, et al. *Am. J. Pathol.* 2007, 171, 715-727.
23. Hersh, et al. (2008) *Proc Am Thorac Soc.* 5(4), 486-493.
24. Ishii, et al. (2000). *Eur J Clin Invest*, 30(6), 543-548.
25. Poller, et al. (1992). *Lancet*, 339(8808), 1538.
26. Furie, et al. *J. Clin. Invest.* 2005, 115, 3355-3362.
27. Fay, et al. *Arterioscler. Thromb. Vasc. Biol.* 2007, 27, 1231-1237.
28. Tapson, V. F. *Proc. Am. Thorac. Soc.* 2005, 2, 71-77.
29. Voelkel, et al. (2007). *Chest*, 131(3), 874-879.
30. Yanbaeva, et al. *Chest* 2007, 131, 1557-1566.
31. Rosenberg, et al. (1987). *Hum Pathol*, 18(3), 253-262.
32. Carpenter, S. L., & Mathew, P. (2008). *Haemophilia*, 14(6), 1250-1254.
33. Ribeiro-Oliveira, et al. (2008). *Vasc Health Risk Manag.* 4(4), 787-803.
34. Kumar, et al. (2008). *Curr Opin Nephrol Hypertens*, 17(2), 168-173.
35. Lalouel, et al. (2001). *J Am Soc Nephrol*, 12(3), 606-615.
36. Sevenoaks, M. J., & Stockley, R. A. (2006). *Respir Res.* 7, 70.
37. Wouters, et al. (2002). *Chest*, 121(5 Suppl), 127S-130S.
38. Marcovina, S., & Packard, C. J. (2006). *J Intern Med*, 259(5), 437-446.
39. Qin, et al. (1998). *Am J Physiol*, 274(5 Pt 2), H 1836-1840.
40. Lee, et al. *Crit. Care Med.* 2007, 35, 849-855.
41. Chung, K. F. (2001). *Eur Respir J Suppl*, 34, 50s-59s.
42. Karadag, et al. (2008). *Lung*, 186(6), 403-409.
43. Walter, et al. *Chest* 2008, 133, 19-25. 38.
44. Wilk, et al. (2007). *BMC Med Genet*, 8 Suppl 1, S8.
45. Lee, et al. (2008). *Respir Med*, 102(9), 1311-1320.
46. Lappalainen, et al. (2005). *Am J Respir Cell Mol Biol*, 32(4), 311-318.
47. Bolton, et al. (2007). *COPD.* 4(2), 121-126.
48. Tiengo, et al. (2008). *Diabetes Metab*, 34(5), 447-454.
49. Celli, et al. (2004). *N Engl J Med*, 350(10), 1005-1012.
50. Pasa-Tolic, et al. *Biotechniques* 2004, 37, 626-633.
51. Anderson, et al. In: Valafar F., Valafar H. (Eds.). *Proceedings of the International Conference on Mathematics and Engineering Techniques in Medicine and Biological Sciences* (METMBS '04), CSREA Press, Las Vegas 2004, pp. 151-156.
52. Smith, et al. *Proteomics* 2002, 2, 513-523.
53. Adkins, et al. *Proteomics* 2005, 5, 3454-3466.
54. Qian, et al. *Proteomics* 2005, 5, 572-584.
55. Belov, et al. *J. Am. Soc. Mass Spectrom.* 2004, 15, 212-232.

56. Eng, J et al. *J. Am. Soc. Mass Spectrom.* 1994, 5, 976-989.
57. Link, et al. *Nat. Biotechnol.* 1999, 17, 676-682.
58. Washburn, et al. *Nat. Biotechnol.* 2001, 19, 242-247.
59. Rocke, et al. *J. Comput. Biol.* 2001, 8, 557-569.
60. Donaldson, et al. *Chest* 2005, 128, 1995-2004.
61. Gan, et al. *Thorax* 2004, 59, 574-580.
62. Wedzicha, et al. *Thromb. Haemost.* 2000, 84, 210-215.
63. Rennard, S. I. *Am. J. Respir. Crit. Care Med.* 1999, 160, S12-S16.
64. Celli, et al. *Proc. Am. Thorac. Soc.* 2006, 3, 461-465.
65. Feghali-Bostwick, et al. *Am. J. Respir. Crit. Care Med.* 2007, 177, 156-163.
66. Thyagarajan, et al. *Int. J. Epidemiol.* 2006, 35, 1001-1008.
67. Cupples, et al. *BMC Med. Genet.* 2007, 8, S1.
68. Volanakis, J. E. *Annu. Rev. Immunol.* 1995, 13:277-305, 277-305.
69. Liu, et al. *J. Biol. Chem.* 2001, 276, 34686-34694.
70. Jourdain, et al. *Am. J. Respir. Crit. Care Med.* 1997, 156, 1825-1833.
71. Ashitani, et al. *Intern Med.* 2002, 41, 181-185.
72. Alessandri, et al. *Thromb. Haemost.* 1994, 72, 343-346.
73. Stockley, R. A. (2007). *Thorax,* 62(8), 657-660.
74. Elias, J. E. & Gygi, S. P. (2007) *Nature Methods,* 4(3), 207-214.

The invention claimed is:

1. A method of providing a diagnosis and prognosis of a subject having, or suspected of having, chronic obstructive pulmonary disease (COPD), and of treating the subject, comprising:
making a determination of five or more different proteins in Table 7, or peptides of five or more different proteins in Table 7, in a biological sample from a subject, said method optionally comprising making a determination of one or more proteins in Tables 2, 4, 5 and/or 6, or one or more peptides of one or more proteins in Tables 2, 4, 5 and/or 6, and providing said diagnosis and prognosis of COPD based on the abundance of the five or more different proteins in Table 7; and
consistent with the determination, providing a diagnosis of the subject as either having COPD or not having COPD;
wherein, when the subject is diagnosed as having COPD, a prognosis of rapid or slow decline in lung function is provided and the subject is treated by administering one or more therapeutics selected from immunosuppressants, corticosteroids, 0 2-adrenergic receptor agonists, anticholinergics, and oxygen;
wherein said determination is conducted by measuring the amount of one or more peptides that each comprise 7 to 50 amino acids from each of the five or more different proteins in Table 7; and
wherein said biological sample is plasma prepared from blood where the plasma has been depleted of its most abundant protein.

2. The method of claim 1, comprising making a determination of eight or more different proteins or peptides from different proteins in Table 7.

3. The method of claim 1, wherein the diagnosis and prognosis is rapid decline COPD with an average annual loss of $FEV_1$ of 1.6% or more per year.

4. The method of claim 1, wherein the diagnosis and prognosis is slow decline COPD with an average annual loss of $FEV_1$ of 0.8% or less per year.

5. The method of claim 1, wherein said determination is conducted by measuring or observing the quantity or concentration of one or more nucleic acids expressed from a gene encoding one or more different proteins or peptides of proteins in Tables 2, 4, 5 6 and/or 7.

6. The method of claim 1, wherein said diagnosis and prognosis is:
(a) a diagnosis and prognosis of rapid decline in lung function relative to individuals not having lung disease, said method further comprising making a determination of one or more proteins in any of Tables 2, 4, and/or 6(b), or one or more peptides of the proteins in any of Tables 2, 4, and/or 6(b) in said sample;
(b) a diagnosis and prognosis of slow decline in lung function relative to individuals not having lung disease, said method further comprising making a determination of one or more proteins in any of Tables 2, 4, and/or 6(c), or one or more peptides of the proteins in any of Tables 2, 4, and/or 6(c) in said sample; or
(c) a diagnosis and prognosis of rapid decline in lung function relative to individuals having a slow decline in lung function, said method further comprising making a determination of one or more proteins in any of Tables 2, 4, 5 and/or 6(d), or one or more peptides of the proteins in any of Tables 2, 4, 5 and/or 6(d) in said sample.

7. The method of claim 1, further comprising making a determination of one or more additional proteins, or peptide fragments thereof, selected from the group consisting of: proinsulin, plasminogen, fibrinogen alpha polypeptide, interleukin 6, coagulation factor II, interleukein 1 beta, signal transducer and activator of transcription 3, cyclin dependent kinase 2, family with sequence similarity 3 member A (FAM3A), and peptide fragment of any of the foregoing.

8. A composition comprising five or more nucleic acid molecules comprising a nucleotide sequence encoding the proteins and/or peptides of those proteins recited in Table 7, or a complementary nucleotide sequence thereof, wherein said composition does not comprise nucleic acids encoding all proteins recited in Table 7 or their complementary sequences.

9. The composition of claim 8, wherein said composition is in the form of an array having the five or more nucleic acids attached to spatially addressable locations.

10. A method of providing a diagnosis and prognosis of a subject having or suspected of having COPD and of treating and following the course of COPD progression in a subject having COPD comprising:
(a) making a first determination at a first time, of one or more peptide fragments of five proteins identified in Table 7 in a first sample from the subject;
(b) consistent with the determination, providing a diagnosis of the subject as either having COPD, or not having COPD; wherein, when the subject is diagnosed as having COPD, further providing a prognosis of rapid or slow decline in lung function;
(c) making a second determination of at least the same proteins or peptide fragments from a second sample obtained from the subject at a second time; and
(d) comparing the first determination to the second determination to determine the progression or regression of COPD;
wherein, when the subject is diagnosed as having COPD, administering to the subject at least one therapeutic agent selected from the group consisting of immunosuppressants, corticosteroids, β2-adrenergic receptor agonists, anticholinergics, and/or oxygen;
wherein said or one or more peptide fragments each comprise 7 to 50 amino acids; and
wherein said first and second biological samples are plasma prepared from blood where the plasma has been depleted of its most abundant protein.

11. The method of claim 10, wherein at least one therapeutic agent, selected from the group consisting of immunosuppressants, corticosteroids, β2-adrenergic receptor agonists, and anticholinergics, is administered to said subject.

12. The method of claim 11, wherein said first sample was obtained from said subject before said second sample, and wherein said therapeutic agent is administered after said first sample was obtained from said subject, and before said second sample was obtained from said subject.

13. The method of claim 12, wherein said therapeutic agent is selected from the group consisting of: corticosteroids, β2 adrenergic receptor agonists, and anticholinergics.

14. The method of claim 12, further comprising changing the treatment of a subject based upon said diagnosis and prognosis.

15. The method of claim 1, wherein said determination is conducted with tryptic peptides of five or more proteins in Table 7.

16. The method of claim 10, wherein said first determination is conducted with tryptic peptides of five or more proteins in Table 7.

17. The method of claim 12, wherein said first determination is conducted with tryptic peptides of five or more proteins in Table 7.

18. A method of providing a diagnosis and prognosis of a subject having, or suspected of having, chronic obstructive pulmonary disease (COPD), and of treating the subject, comprising:
making a determination of five or more different proteins in Table 7, or peptides of five or more different proteins in Table 7, in a biological sample from a subject; said method comprising making a determination of one or more additional proteins in Tables 2, 4, 5 and/or 6, or one or more peptides of one or more proteins in Tables 2, 4, 5 and/or 6, and providing said diagnosis or prognosis of COPD based on the abundance of the five or more different proteins in Table 7; and
consistent with the determination, providing a diagnosis of the subject as either having COPD, or not having COPD;
wherein, when the subject is diagnosed as having COPD, a prognosis of rapid or slow decline in lung function is provided and the subject is treated by administering one or more therapeutic agents selected from immunosuppressants, corticosteroids, β2 -adrenergic receptor agonists, anticholinergics, and oxygen;
wherein said or one or more peptides each comprise 7 to 50 amino acids; and
wherein said biological sample is plasma prepared from blood where the plasma has been depleted of its most abundant protein.

19. A method of providing a diagnosis and prognosis of a subject having or suspected of having COPD and of treating and following the course of COPD in a subject having COPD comprising:
(a) making a first determination, at a first time, of at least five proteins or peptide fragments of five proteins identified in Table 7 in a first sample from the subject;
(b) consistent with the determination, providing a diagnosis of the subject as either having COPD, or not having COPD; wherein, when the subject is diagnosed as having COPD, further providing a prognosis of rapid or slow decline in lung function;
(c) making a second determination of at least the same proteins or peptide fragments from a second sample obtained from the subject at a second time; and
(d) comparing the first determination to the second determination to determine the progression or regression of COPD;
wherein, when the subject is diagnosed as having COPD, administering to the subject at least one therapeutic agent selected from the group consisting of immunosuppressants, corticosteroids, β2-adrenergic receptor agonists, anticholinergics, and/or oxygen;
wherein said peptide fragments each comprise 7 to 50 amino acids; and
wherein said first and second biological samples are plasma prepared from blood where the plasma has been depleted of its most abundant protein.

20. A composition comprising:
a) an array having five or more proteins identified in Table 7 or peptide fragments of five or more proteins identified in Table 7 attached to five or more different spatially addressable locations of the array; or
b) an array having five or more antibodies or antigen binding fragments thereof that bind peptides of five or more proteins in Table 7 attached to five or more different spatially addressable locations of the array.

21. The composition of claim 20, wherein at least one of the proteins, peptides, antibodies or antigen binding fragments is covalently bound to said array.

* * * * *